United States Patent
Ezzelarab et al.

(10) Patent No.: US 11,022,601 B2
(45) Date of Patent: Jun. 1, 2021

(54) USE OF EOMESODERMIN TO DETERMINE RISK OF ALLOGRAFT REJECTION

(71) Applicant: University of Pittsburgh—Of the Commonwealth System of Higher Education, Pittsburgh, PA (US)

(72) Inventors: Mohamed B. Ezzelarab, Pittsburgh, PA (US); Angus W. Thomson, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/545,414

(22) PCT Filed: Jan. 22, 2016

(86) PCT No.: PCT/US2016/014507
§ 371 (c)(1),
(2) Date: Jul. 21, 2017

(87) PCT Pub. No.: WO2016/118852
PCT Pub. Date: Jul. 28, 2016

(65) Prior Publication Data
US 2018/0045710 A1 Feb. 15, 2018

Related U.S. Application Data

(60) Provisional application No. 62/106,834, filed on Jan. 23, 2015.

(51) Int. Cl.
*G01N 33/50* (2006.01)

(52) U.S. Cl.
CPC . *G01N 33/5005* (2013.01); *G01N 2333/4703* (2013.01)

(58) Field of Classification Search
None
See application file for complete search history.

(56) References Cited

U.S. PATENT DOCUMENTS

| | | |
|---|---|---|
| 7,026,121 B1 | 4/2006 | Wohlgemuth et al. |
| 2006/0088836 A1* | 4/2006 | Wohlgemuth ....... C12Q 1/6881 435/6.14 |
| 2015/0299656 A1* | 10/2015 | Gattinoni ............... A61K 35/17 424/93.71 |

FOREIGN PATENT DOCUMENTS

| | | |
|---|---|---|
| WO | WO 2006/125301 | 11/2006 |
| WO | WO 2015/035367 | 3/2015 |

OTHER PUBLICATIONS

Popescu et al., T-bet:Eomes Balance, Effector Function, and Proliferation of Cytomegalovirus-Specific CD8+ T Cells during Primary Infection Differentiates the Capacity for Durable Immune Control; Journal of Immunology, 1401436, pp. 1-15, published online Oct. 22, 2014.*
McLane et al., Differential Localization of T-bet and Eomes in CD8 T Cell Memory Populations; Journal of Immunology; vol. 190, pp. 3207-3215, 2013 (Year: 2013).*
Allanach et al., Comparing Microarray Versus RT-PCR Assessment of Renal Allograft Biopsies: Similar Performance Despite Different Dynamic Ranges; American Journal of Transplantation, vol. 8, pp. 1006-1015, 2008 (Year: 2008).*
Kurtulus et al., Protecting and rescuing the effectors: roles of differentiation and survival in the control of memory T cell development; Immunology, vol. 3, No. 404, pp. 1-13, 2013 (Year: 2013).*
Banerjee et al., "The Transcription Factor Eomesodermin Enables CD8+ T Cells to Compete for the Memory Cell Niche," *J. Immunol.*, vol. 185:4988-4992, 2010.
Du Rocher et al., "Eomesodermin Regulates the Early Activation of Alloreactive CD4 T Cells and is Critical for Both Gvh and GVL Responses," *Blood*, vol. 122:133, 2013 (http://www.bloodjournal.org/content/122/21/133).
Ezzelarab et al., "Eomesodermin$^{lo}$ CTLA4$^{hi}$ Alloreactive CD8$^+$ Memory T Cells are Associated with Prolonged Renal Transplant Survival Induced by Regulatory Dendritic Cell Infusion in CTLA4I-Treated Non-Human Primates," *Transplantation*, vol. 100(1):91-102, 2016.
Ezzelarab et al., "Eomesodermin Expression by Alloreactive Non-Human Primate CD8+ Memory T Cells: Influence of CTLA4Ig and Regulatory DC Infusion in Renal Allograft Recipients," (Abstract), *Am. J. Transplant.*, vol. 15 (Suppl 3), 2015.
Hegel et al., "CD152 (CTLA-4) Regulates Effector Functions of CD8$^+$ T Lymphocytes by Repressing Eomesodermin," *Eur. J. Immunol.*, vol. 39:883-893, 2009.
Iancu et al., "Persistence of EBV Antigen-Specific CD8 T Cell Clonotypes during Homeostatic Immune Reconstitution in Cancer Patients," *PLoS One*, vol. 8:e78686, 2013.

* cited by examiner

*Primary Examiner* — Antonio Galisteo Gonzalez
(74) *Attorney, Agent, or Firm* — Klarquist Sparkman, LLP

(57) ABSTRACT

Pre-existing alloreactive memory T cells are a major barrier to the induction of allograft tolerance in organ transplant recipients. The use of Eomesodermin (Eomes) expression in memory T cells to determine the risk of allograft rejection in a subject is described. Also described is the use of Eomes expression in memory T cells of transplant recipients to modify immunosuppressive therapy.

12 Claims, 22 Drawing Sheets

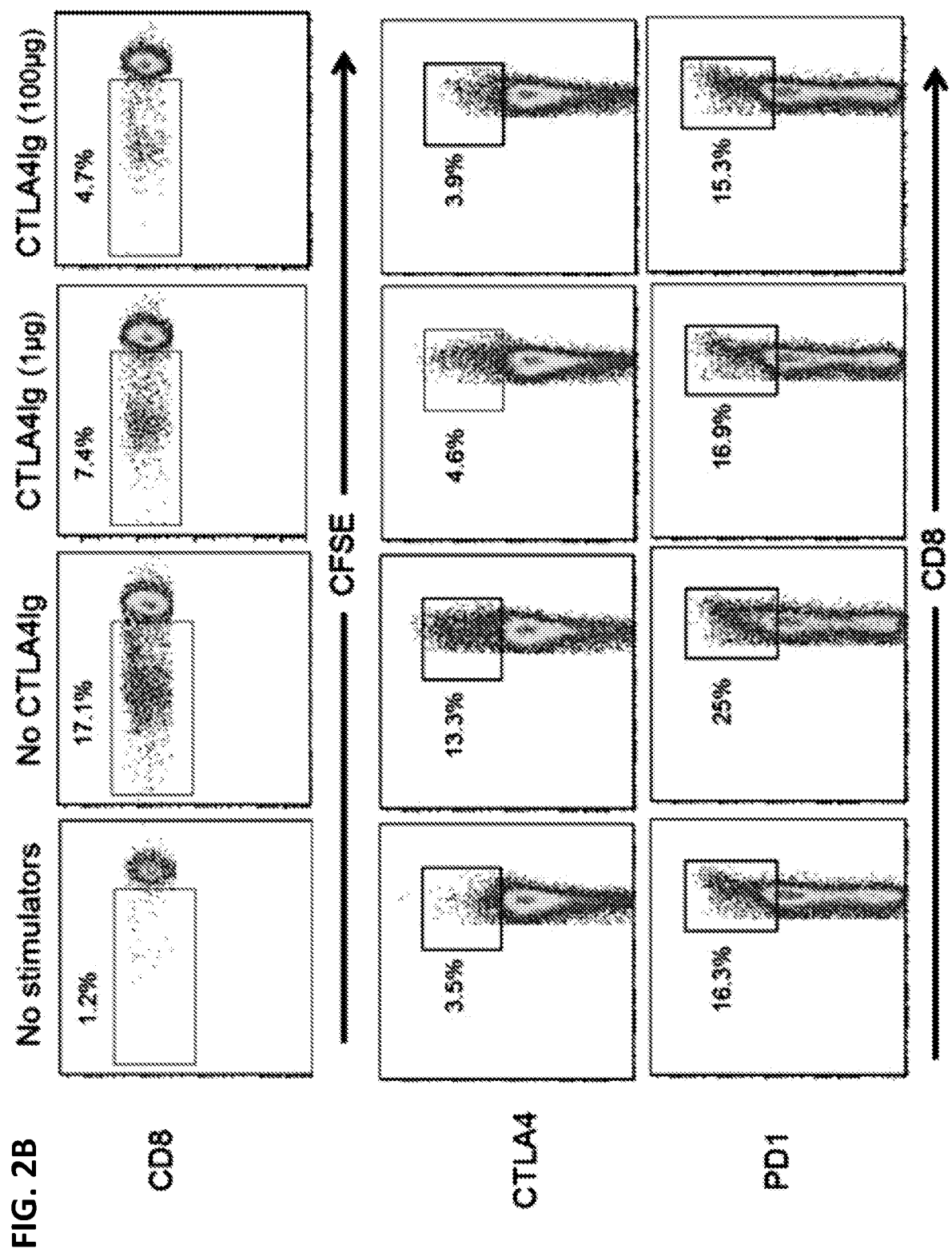

US 11,022,601 B2

USE OF EOMESODERMIN TO DETERMINE RISK OF ALLOGRAFT REJECTION

CROSS REFERENCE TO RELATED APPLICATIONS

This application is the U.S. National Stage of International Application No. PCT/US2016/014507, filed Jan. 22, 2016, published in English under PCT Article 21(2), which claims the benefit of U.S. Provisional Application No. 62/106,834, filed Jan. 23, 2015, which is herein incorporated by reference in its entirety.

ACKNOWLEDGMENT OF GOVERNMENT SUPPORT

This invention was made with government support under grant number AI051698 awarded by the National Institutes of Health. The government has certain rights in the invention.

FIELD

This disclosure concerns measuring Eomesodermin (Eomes) expression in memory T cells to determine a transplant patient's risk for allograft rejection and to modify treatment options, such as immunosuppressive therapy.

BACKGROUND

Induction of tolerance to organ allografts can be readily achieved in rodents by a variety of strategies. However, such approaches have proved unsuccessful in non-human primate (NHP) models and in clinical transplantation. Pre-existing alloreactive memory T cells (Tmem) are considered a major barrier to the induction of tolerance (Valujskikh and Li, *J Am Soc Nephrol* 18(8):2252-2261, 2007). In NHP studies, kidney allograft rejection is associated with the development of co-stimulation blockade (CB)-resistant Tmem (Kean et al., *Am J Transplant* 7(2):320-335, 2007; Larsen et al., *Am J Transplant* 10(11):2396-2409, 2010; Page et al., *Am J Transplant* 12(1):115-125, 2012). Recent clinical testing of CTLA4Ig (belatacept), a chimeric fusion protein that blocks the B7-CD28 pathway, in a calcineurin inhibitor-free regimen, has resulted in an increased incidence of acute cellular rejection in renal transplant recipients (Vincenti et al., *Am J Transplant* 10(3):535-546, 2010; Pestana et al., *Am J Transplant* 12(3):630-639, 2012). There is also evidence that CTLA4Ig may prevent regulatory T cell (Treg)-dependent transplant tolerance in rodents (Charbonnier et al., *Am J Transplant* 12(9):2313-2321, 2012; Riella et al., *Am J Transplant* 12(4):846-855, 2012).

Alloreactive $CD8^+$ Tmem are known to be more resistant to CB than $CD4^+$ Tmem (Ferrari-Lacraz et al., *J Immunol* 167(6):3478-3485, 2001; Trambley et al., *J Clin Invest* 104(12):1715-1722, 1999; Ferrari-Lacraz et al., *Transplantation* 82(11):1510-1517, 2006; Kitchens et al., *Am J Transplant* 12(1):69-80, 2012). Eomesodermin (Eomes) is a key transcription factor in $CD8^+$ Tmem differentiation, fate and function (Pearce et al., *Science* 302(5647):1041-1043, 2003; Intlekofer et al., *Nat Immunol* 6(12):1236-1244, 2005). It plays a critical role in the long-term survival of antigen (Ag)-specific central memory T cells (Tcm) (Banerjee et al., *J Immunol* 185(9):4988-4992, 2010). However, the role of Eomes in the differentiation, regulation and maintenance of donor-specific Tmem in allograft recipients has not been previously examined.

SUMMARY

It is disclosed herein that expression of Eomes in memory T cells can be used to predict the risk of allograft rejection. Memory T cell expression of Eomes can also be used to monitor and modify immunosuppressive therapy administered to a subject after an organ transplant.

Provided is a method of determining the risk of allograft rejection in a subject. In some embodiments, the method includes providing a peripheral blood mononuclear cell (PBMC) sample from the subject; measuring expression of Eomes in memory T cells present in the sample; and determining an increased risk for allograft rejection in the subject if expression of Eomes is increased in the memory T cells compared to expression of Eomes in control memory T cells. In some examples, Eomes expression is measured before and after organ transplant to determine the risk of allograft rejection. In other examples, Eomes expression is measured before transplant, but following contact of a subject's memory T cells with donor-derived cells ex vivo.

In some embodiments, the method further includes modifying immunosuppressive therapy for the subject if an increase in Eomes expression is detected. In some examples, the current immunosuppressive therapy is increased in dose and/or frequency. In other examples, an alternative or additional immunosuppressive therapy is administered to the subject.

Also provided is a method of treating a subject that has received an allograft. In some embodiments, the method includes administering an immunosuppressive therapy to the subject; providing a PBMC sample obtained from the subject before administration of the immunosuppressive therapy and a PBMC sample obtained from the subject after administration of the immunosuppressive therapy; detecting an increase in expression of Eomes in memory T cells of the sample obtained after administration of the immunosuppressive therapy compared to the sample obtained before administration of immunosuppressive therapy; and modifying the immunosuppressive therapy administered to the subject. In some examples, modifying the immunosuppressive therapy includes increasing the dose and/or frequency of the immunosuppressive therapy administered to the subject. In some examples, modifying the immunosuppressive therapy includes administering to the subject an alternative or additional immunosuppressive therapy.

In other embodiments, the method of treating a subject that has received an allograft includes providing a PBMC sample obtained from the subject before receiving the allograft and a PBMC sample obtained from the subject after receiving the allograft; detecting an increase in expression of Eomes in memory T cells of the sample obtained after receiving the allograft compared to the sample obtained before receiving the allograft; and administering an immunosuppressive therapy to the subject.

The foregoing and other objects, features, and advantages of the invention will become more apparent from the following detailed description, which proceeds with reference to the accompanying figures.

BRIEF DESCRIPTION OF THE DRAWINGS

(FIG. 1A) Left, expression of Eomes by total $CD4^+$ and $CD8^+$ peripheral blood T cells in a representative normal rhesus monkey determined by flow cytometry. Right, individual and mean values for 8 normal monkeys are also shown. (FIG. 1B)

Eomes expression by CD4+ and CD8+ naive and memory T cell subsets, determined by differential CD45RA and CD28 expression: central memory T cells (Tcm; CD45RA−CD28+), naïve T cells (Tn; CD45RA+CD28+), effector memory T cells (Tem; CD45RA−CD28−) and effector T cells (Teff; CD45RA+CD28−). (FIG. 1C) Individual and mean incidences of Eomes+ CD4+ and CD8+ T naïve and memory cell subtypes (n=6 normal monkeys). (FIG. 1D) Eomes versus CTLA4 expression by CD4+ and CD8+ naïve and memory T cell subsets in naïve monkeys (data representative of n=4 monkeys). (FIG. 1E) CD122 (IL-2Rβ), CD45RA, CCR7, PD1, CD25 and Foxp3 expression by $Eomes^{lo}CTLA4^{hi}$ versus $Eomes^{hi}CTLA4^{lo}CD8^+$ T cells in naïve monkeys. Representative data (upper) and means+1 SD for n=4 monkeys (lower) are shown; ns=not significant.

FIGS. 2A-2C: Effect of CD28 co-stimulation blockade with CTLA4Ig on PD1 and CTLA4 expression by allostimulated normal monkey CD8+ T cells. (FIG. 2A) Percentages of PD1+ and CTLA4+ populations in total memory (CD95+) CD4+ and CD8+ T cells obtained from peripheral blood of 6 normal monkeys. (FIG. 2B) CTLA4Ig inhibits CD8+ T cell proliferation (upper panel) and upregulation of CTLA4 and PD1 expression (lower panels) in a concentration-dependent manner Responder PBMC were co-cultured with allogeneic T cell-depleted stimulator PBMC in carboxyfluorescein succinimidyl ester (CFSE)-mixed leukocyte reaction (MLR) for 5 days, in the absence or presence of CTLA4Ig (1 or 100 µg/ml). CFSE dilution and percentages of CTLA4+ and PD1+ populations were determined after gating on CD8+ T cells. (FIG. 2C) Percentages of CD8+PD1+ and CD8+ CTLA4+ T cells following allostimulation in the absence or presence of CTLA4Ig. Bars represent means+1 SD (n=5 independent experiments); ns=not significant.

(FIG. 3A) Eomes expression by normal monkey CD8+ T cells following allostimulation in MLR, in the presence or absence of CTLA4Ig. Representative data from one experiment is shown (top). CTLA4 and Eomes expression by CD8+ T cells following allostimulation is also shown (bottom panels). Representative and mean values+1 SD of 4 independent experiments are shown; ns=not significant. (FIG. 3B) Frequencies of $Eomes^{lo}CTLA4^{hi}$ and $Eomes^{hi}CTLA4^{lo}$ CD8+ T cells following allostimulation in the absence or presence of CTLA4Ig. Representative data (top) and means+1 SD of 4 independent experiments are shown (bottom).

(FIG. 4A) Proliferation of $Eomes^{hi}$ and $Eomes^{lo}$ CD4+ and CD8+ T cells following allostimulation in CFSE-MLR. Histograms show CTLA4 expression by proliferating cells (values in parentheses indicate MFI). Grey histograms indicate isotype controls. (FIG. 4B) Left, proliferation of $Eomes^{hi}$ compared with $Eomes^{lo}CD8^+$ T cells; right, CTLA4 expression (MFI) by proliferating $Eomes^{lo}$ and $Eomes^{hi}CD8^+$ T cells. Responder PBMC were co-cultured with allogeneic T cell-depleted PBMC for 5 days in CFSE-MLR. Proliferation of $Eomes^{hi}$ and $Eomes^{lo}$ T cell populations were determined after gating on CD4+ or CD8+ T cells. (n=10 normal monkeys).

(FIG. 5A) Frequencies of $Eomes^{hi}CTLA4^{lo}$ and $Eomes^{lo}CTLA4^{hi}$ CD8+ T cell subpopulations in MLR. Data are from a representative normal monkey. (FIG. 5B) left, combined data from 8 allogeneic monkey stimulator-responder combinations; right, frequencies of memory and naïve T cell subtypes in the $Eomes^{lo}CTLA4^{hi}$ CD8+ T subpopulation after allostimulation. The combined data are from 8 different allogeneic monkey responder and stimulator pairs.

(FIG. 7A) Incidences of $Eomes^{lo}CTLA4^{hi}$ and $Eomes^{hi}CTLA4^{lo}CD8^+T$ cells in response to donor or 3rd party stimulation, before transplant and on POD28 post-transplant in representative control and DCreg-treated monkeys. (FIG. 7B) Mean values of percentages (top) and absolute numbers (bottom) from 4 allograft recipients from each group. Responder PBMC were co-cultured with donor or third party T cell-depleted PBMC for 5 days. Percentages and absolute numbers of $Eomes^{low}CTLA4^{high}$ were determined after gating on CD8+ T cells.

While Eomes CD8+T cells express lower levels of IL-2, they expressed significantly higher levels of TNFα, Granzyme B, and IFNγ.

Figure 12A:
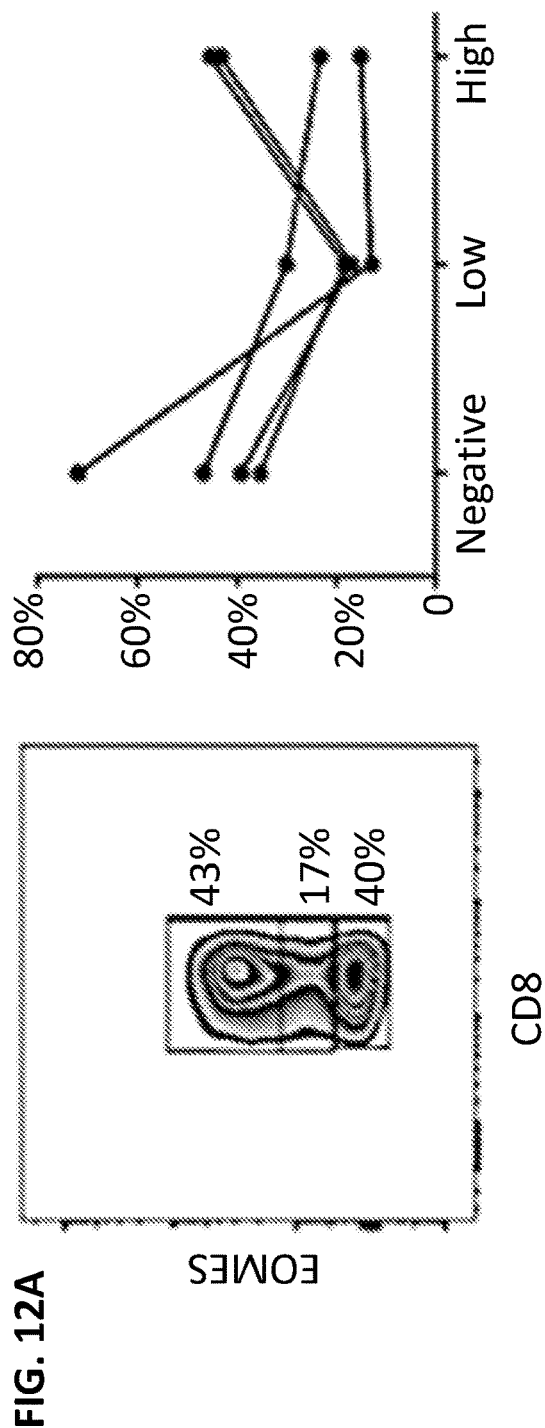
Figure 12B:
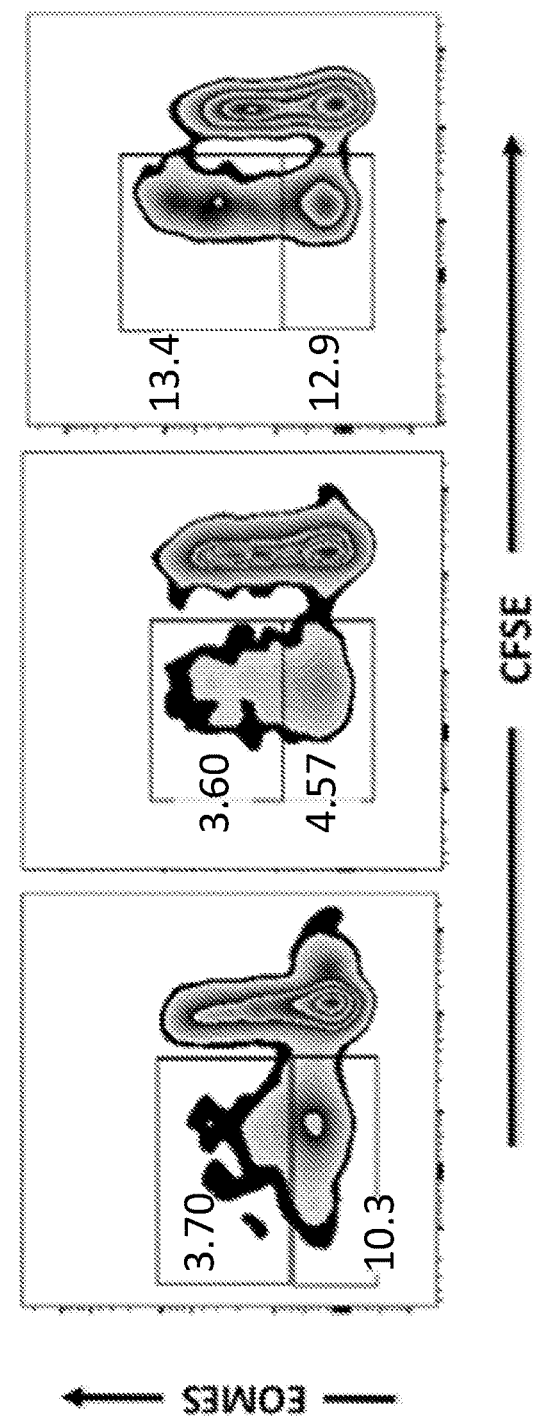

FIGS. 12A-12B: Humans exhibit variable degrees of Eomes expression by CD8+T cells, particularly after allogeneic antigen stimulation. (FIG. 12A) Human CD8+T cells were stained for Eomes by flow cytometry (left). PBMC were obtained from healthy volunteers. Gating was based on isotype control. Data from 4 different human subjects are presented. (FIG. 12B) Eomes expression by human T cells stimulated with allogeneic T cell-depleted PBMC in co-culture for 5 days. Responder T cells were CFSE-labeled before co-culture. Percent proliferation was determined by CFSE dye dilution.

DETAILED DESCRIPTION

I. Abbreviations

Ag antigen
CB co-stimulation blockade
CFSE carboxyfluorescein succinimidyl ester
CTLA4 co-inhibitory cytotoxic T lymphocyte Ag 4
DCreg regulatory dendritic cell
Eomes Eomesodermin
FACS fluorescence activated cell sorting
IFNγ interferon gamma
IL interleukin
MFI mean fluorescence intensity
MLR mixed leukocyte reaction
NHP non-human primate
PBMC peripheral blood mononuclear cell
PD1 programmed death-1
POD post-operative days
RT room temperature
T-bet T-box expressed in T cells
Tcm central memory T cells
Teff effector T cells
Tem effector memory T cells
Tmem memory T cells
Tn naïve T cells
TNFα tumor necrosis factor alpha
Treg regulatory T cells II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Allograft: A transplant of an organ, tissue, bodily fluid or cell from one individual to a genetically non-identical individual of the same species.

Allograft rejection: A partial or complete immune response to a transplanted cell, tissue, organ, or the like on or in a recipient of the transplant due to an immune response to the allograft. Allografts can be rejected through either a cell-mediated or humoral immune reaction of the recipient against histocompatibility antigens present on the donor cells.

Eomesodermin (Eomes): A transcription factor that is important for embryonic development of mesoderm and the central nervous system in vertebrates. Eomes also plays a key role in CD8+ Tmem differentiation, fate and function. This transcription factor also plays a critical role in the long-term survival of antigen-specific central memory T cells (Tcm). The gene encoding Eomes belongs to the TBR1 (T-box brain protein 1) sub-family of T-box genes that share the common DNA-binding T-box domain (see NCBI Gene ID 8320).

Immunosuppressant: Any compound that decreases the function or activity of one or more aspects of the immune system, such as a component of the humoral or cellular immune system or the complement system Immunosuppressants are also referred to as "immunosuppressive agents."

Known immunosuppressants include, but are not limited to: (1) antimetabolites, such as purine synthesis inhibitors (e.g., azathioprine and mycophenolic acid), pyrimidine synthesis inhibitors (e.g., leflunomide and teriflunomide) and antifolates (e.g., methotrexate); (2) macrolides, such as FK506, cyclosporine A and pimecrolimus; (3) TNF-α inhibitors, such as thalidomide and lenalidomide; (4) IL-1 receptor antagonists, such as anakinra; (5) mammalian target of rapamycin (mTOR) inhibitors, such as rapamycin (sirolimus), deforolimus, everolimus, temsirolimus, zotarolimus and biolimus A9; (6) corticosteroids, such as prednisone; and (7) antibodies to any one of a number of cellular or serum targets.

Exemplary cellular targets and their respective inhibitor compounds include, but are not limited to complement component 5 (e.g., eculizumab); tumor necrosis factors (TNFs) (e.g., infliximab, adalimumab, certolizumab pegol, afelimomab and golimumab); IL-5 (e.g., mepolizumab); IgE (e.g., omalizumab); BAYX (e.g., nerelimomab); interferon (e.g., faralimomab); IL-6 (e.g., elsilimomab); IL-12 and IL-13 (e.g., lebrikizumab and ustekinumab); CD3 (e.g., muromonab-CD3, otelixizumab, teplizumab, visilizumab); CD4 (e.g., clenoliximab, keliximab and zanolimumab); CD11a (e.g., efalizumab); CD18 (e.g., erlizumab); CD20 (e.g., afutuzumab, ocrelizumab, pascolizumab); CD23 (e.g., lumiliximab); CD40 (e.g., teneliximab, toralizumab); CD62L/L-selectin (e.g., aselizumab); CD80 (e.g., galiximab); CD147/basigin (e.g., gavilimomab); CD154 (e.g., ruplizumab); BLyS (e.g., Belimumab); CTLA-4 (e.g., ipilimumab, tremelimumab); CAT (e.g., bertilimumab, lerdelimumab, metelimumab); integrin (e.g., natalizumab); IL-6 receptor (e.g., Tocilizumab); LFA-1 (e.g., odulimomab); and IL-2 receptor/CD25 (e.g., basiliximab, daclizumab, inolimomab).

Other immunosuppressive agents include zolimomab aritox, atorolimumab, cedelizumab, dorlixizumab, fontolizumab, gantenerumab, gomiliximab, maslimomab, morolimumab, pexelizumab, reslizumab, rovelizumab, siplizumab, talizumab, telimomab aritox, vapaliximab, vepalimomab, anti-thymocyte globulin, anti-lymphocyte globulin; CTLA-4 inhibitors (e.g., abatacept, belatacept); aflibercept; alefacept; rilonacept; and TNF inhibitors (e.g., etanercept).

Immunosuppressive therapy: A treatment that reduces the activity or function of the immune system.

Isolated: An "isolated" biological component, such as a nucleic acid, protein or cell, has been substantially separated or purified away from other biological components in the environment in which the component naturally occurs, i.e., other cells, chromosomal and extra-chromosomal DNA and RNA, proteins and organelles.

Memory T cells (Tmem): A subset of T lymphocytes that have previously encountered and responded to their cognate antigen. In some embodiments, Tmem are identified as CD95$^+$ and/or CD45RO$^+$. Memory T cells include, but are not limited to, central memory T cells (Tcm) and effector memory T cells (Tem), which can be distinguished based on differential expression of several proteins. Tcm cells are CD45RA$^-$CD45RO$^+$CCR7$^+$CD62L$^+$, while Tem cells are CD45RA$^-$CD45RO$^+$CCR7$^-$CD62L$^-$. In addition, Tcm cells secrete IL-2 and Tem cells produce effector cytokines such as IFNγ and IL-4.

Subject: Living multi-cellular vertebrate organisms, a category that includes both human and non-human mammals. In some examples, a subject is a transplant recipient (for example a subject that has received an organ transplant, such as a liver, heart, lung, or kidney transplant), or a candidate for a transplant recipient.

Transplant: Graft of an organ, tissue or cells from one subject to another subject.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Using a robust, rhesus monkey model, it has been reported that systemic administration of donor-derived regulatory dendritic cells (DCreg), one week before transplant, together with CTLA4Ig (abatacept) and tapered rapamycin maintenance monotherapy, can significantly prolong renal allograft survival (Ezzelarab et al., *Am J Transplant* 13(8): 1989-2005, 2013). This therapeutic effect of DCreg is associated with increased CD4$^+$ Treg to CD8$^+$ Tmem ratios in the peripheral blood and with upregulation of co-inhibitory cytotoxic T lymphocyte Ag 4 (CTLA4; CD152) and programmed death-1 (PD1; CD279) by Tmem following their stimulation by donor, but not third party Ag. Together, these findings suggest regulation of donor-specific Tmem responses in DCreg recipients (Azimzadeh and Bromberg, *Nat Rev Nephrol* 9(10):557-559, 2013).

Tmem, particularly those resistant to co-stimulation blockade (CB), are a major barrier to transplant tolerance. The transcription factor Eomesodermin (Eomes) is critical for Tmem development. The studies disclosed herein evaluated Eomes and co-inhibitory CTLA4 expression by allo-activated monkey Tmem in the presence of CTLA4Ig, both in vitro and in renal allograft recipients, with or without regulatory dendritic cell (DCreg) infusion. Eomes was expressed more by normal CD8$^+$ than CD4$^+$ T cells. Central Tmem (Tcm) expressed the highest levels. By contrast, CD8$^+$ T cells displayed minimal CTLA4. Following allostimulation, distinct proliferating Eomes$^{lo}$CTLA4$^{hi}$ and Eomes$^{hi}$CTLA4$^{lo}$ CD8$^+$T populations were identified, with a high proportion of Tcm being Eomes$^{lo}$CTLA4$^{hi}$. CB with CTLA4Ig during allostimulation of CD8$^+$T cells reduced CTLA4, but not Eomes expression, leading to significantly reduced Eomes$^{lo}$CTLA4$^{hi}$ cells. After transplantation with CB and rapamycin, donor-reactive Eomes$^{lo}$CTLA4$^{hi}$ CD8$^+$ T cells were reduced significantly. However, in monkeys given DCreg, Eomes$^{lo}$CTLA4$^{hi}$ CD8$^+$T cell levels remained similar to those pre-transplant. In one long-surviving DCreg-treated recipient, Eomes$^{lo}$CTLA4$^{hi}$ CD8$^+$T cells were maintained transiently after immunosuppression withdrawal. CB resistance of donor-reactive Tmem after transplantation may be related to reduction of Eomes$^{lo}$CTLA4$^{hi}$ Tmem. A relative increase in this population may contribute to the ability of DCreg to prolong organ allograft survival in CB-treated recipients.

IV. Overview of Several Embodiments

Pre-existing alloreactive memory T cells are a major barrier to the induction of allograft tolerance in organ transplant recipients. It is disclosed herein that expression of Eomes in memory T cells can be used to predict the risk of allograft rejection. Memory T cell expression of Eomes can also be used to monitor and modify immunosuppressive therapy administered to a subject after an organ transplant.

Provided herein is a method of determining the risk of allograft rejection in a subject. In some embodiments, the method includes providing a PBMC sample from the subject; measuring expression of Eomes in memory T cells present in the sample; and determining an increased risk for allograft rejection in the subject if expression of Eomes is increased in the memory T cells compared to a control, such as compared to expression of Eomes in control memory T cells.

Eomes expression can be measured before and after organ transplant to determine the risk of allograft rejection. Thus, in some examples of the disclosed method, the subject has already received the allograft and the control memory T cells are memory T cells obtained from the subject prior to transplant. In other examples of the method, the subject has already received the allograft and the control memory T cells are memory T cells obtained from a subject that has not received an allograft. In alternative examples, the subject has already received the allograft and expression of Eomes in memory T cells is compared to a set control value.

Eomes expression also can be measured before transplant to predict risk of allograft rejection. Thus, in some examples, the subject has not yet received the allograft and expression of Eomes is measured in the memory T cells after exposure of the memory T cells to donor-derived cells ex vivo. In some cases, the control memory T cells are memory T cells that have not been exposed to donor-derived cells, either non-exposed cells from the subject or from a control subject.

Eomes can also be measured after transplant to predict risk of allograft rejection. In some examples, the subject has already received the allograft and expression of Eomes is measured in memory T cells of the subject after exposure of the memory T cells to donor-derived cells ex vivo. As a control, Eomes expression is detected in recipient memory T cells that have been exposed to third party cells ex vivo.

Eomes expression can also be measured at particular time points after organ transplant as a means to identify a subject that is a candidate for being weaned off immunosuppressive therapy. A subject with relatively low (compared to a control or standard value) level of Eomes expression would be a good candidate for being weaned off immunosuppressive therapy because the subject would be less likely to reject the allograft.

Also provided is a method of treating a subject that has received an allograft. In some embodiments, the method includes administering an immunosuppressive therapy to the subject; providing a PBMC sample obtained from the subject before administration of the immunosuppressive therapy and a PBMC sample obtained from the subject after administration of the immunosuppressive therapy; detecting an increase in expression of Eomes in memory T cells of the sample obtained after administration of the immunosuppressive therapy compared to the sample obtained before administration of immunosuppressive therapy; and modifying the immunosuppressive therapy administered to the subject. In some examples, modifying the immunosuppressive therapy includes increasing the dose and/or frequency of the immunosuppressive therapy administered to the subject. In some examples, modifying the immunosuppressive therapy includes administering to the subject an alternative or additional immunosuppressive therapy.

In other embodiments, the method of treating a subject that has received an allograft includes providing a PBMC sample obtained from the subject before receiving the allograft and a PBMC sample obtained from the subject after receiving the allograft; detecting an increase in expression of Eomes in memory T cells of the sample obtained after receiving the allograft compared to the sample obtained before receiving the allograft; and administering an immunosuppressive therapy to the subject.

In some embodiments, measuring expression of Eomes in memory T cells present in the sample includes isolating memory T cells from the sample and detecting expression of Eomes in the isolated memory T cells. In some examples, isolating memory T cells includes isolating cells that express at least one memory T cell marker, such as CD95 and/or CD45RO. In particular examples, isolating memory T cells further comprises detecting the absence of expression of at least one naïve or effector T cell maker, such as CD28 and/or CD45RA. Methods of detecting protein expression are well-known in the art and include, for example, fluorescence activated cell sorting (FACS) and immunoblot. In some examples, Eomes expression is detected in memory T cells by contacting a sample with an Eomes-specific antibody conjugated to a detectable label, such as a fluorophore.

In other embodiments, measuring expression of Eomes in memory T cells present in the sample includes simultaneously detecting expression of Eomes and at least one memory T cell marker, such as CD95 and/or CD45RO. In some examples, the method further includes simultaneously detecting the absence of expression of at least one naïve or effector T cell marker, such as CD28 and/or CD45RA. Simultaneous detection can be achieved, for example, by cell sorting techniques that are capable of detecting multiple markers at the same time (for example FACS analysis using multiple labeled antibodies that are each specific for a different marker).

In some embodiments, the method further includes modifying immunosuppressive therapy for the subject if an increase in Eomes expression is detected. In some examples, the current immunosuppressive therapy is increased in dose and/or frequency. In other examples, an alternative or additional immunosuppressive therapy is administered to the subject. In other embodiments, the subject is maintained on immunosuppressive therapy (i.e. is not weaned off immunosuppressive therapy) if an increase in Eomes expression is detected.

The disclosed methods can be used to determine the risk of allograft rejection for any type of organ or tissue. In some embodiments, the allograft comprises kidney tissue.

The following examples are provided to illustrate certain particular features and/or embodiments. These examples should not be construed to limit the disclosure to the particular features or embodiments described.

EXAMPLES

It has been reported that CTLA4 may reduce Eomes expression by $CD8^+$ T cells (Hegel et al., *Eur J Immunol* 39(3):883-893, 2009). The studies described below (Examples 1 and 2) examine the expression of Eomes and CTLA4 by normal and allostimulated monkey Tmem and by Tmem in CTLA4Ig-treated renal allograft recipients, without or with DCreg infusion. It was determined that $CD8^+$ T cells express higher levels of Eomes, but lower levels of CTLA4 compared to $CD4^+$ T cells. Tcm expressed the highest levels of Eomes. CD28 blockade with CTLA4Ig significantly reduced CTLA4, but not Eomes expression on alloreactive T cells. These data also show that the combination of CTLA4Ig and pre-transplant DCreg is associated with low Eomes and high CTLA4 expression by donor-reactive $CD8^+$ Tcm, consistent with the reported ability of DCreg infusion to attenuate donor-specific Tmem and prolong graft survival in CB-treated renal allograft recipients.

Example 1: Materials and Methods

This example describes the materials and experimental procedures for the studies described in Example 2.

Experimental Animals

Indian male juvenile rhesus macaques (Macacca mulatta; 5-7 kg) were obtained from the NIAID-sponsored colony (Yemasse, S.C.). Specific environment enrichment was provided.

Renal Transplantation, DCreg Infusion and Immunosuppression

Leukapheresis, generation of donor-derived DCreg and renal transplantation were performed as previously described (Ezzelarab et al., *Am J Transplant* 13(8):1989-2005, 2013; Zahorchak et al., *Transplantation* 84(2):196-206, 2007). Recipient pairs—control (no DC infusion) and experimental animals (DCreg infusion)—received kidney grafts from the same donor. In the experimental group, DCreg ($3.5$-$10 \times 10^6$/kg) were infused intravenously, 7 days before transplantation. All recipients in the control and DCreg groups were given CTLA4Ig (abatacept; Bristol-Myers Squibb; Princeton, N.J.)-based immunosuppression and maintenance rapamycin (Ezzelarab et al., *Am J Transplant* 13(8):1989-2005, 2013).

Mixed Leukocyte Reactions (MLR)

Peripheral blood mononuclear cells (PBMC) were isolated from normal rhesus monkeys for in vitro studies. Unlabeled or carboxyfluorescein succinimidyl ester (CFSE; Molecular Probes, Eugene, Oreg.)-labeled PBMC were used as responders and $CD2^+$T cell-depleted allogeneic irradiated PBMC as stimulators, at a 1:1 ratio. In some MLRs, CTLA4Ig was added (1 µg or 100 µg/ml) at the start of culture. Samples were also obtained from kidney allograft recipient monkeys in a previous study (Ezzelarab et al., *Am J Transplant* 13(8):1989-2005, 2013). Thus, PBMC were also isolated before and after transplantation (post-operative days (POD) 28-56, unless otherwise specified) and co-cultured (Ezzelarab et al., *Am J Transplant* 13(8):1989-2005, 2013) in MLR with either donor or third party stimulator cells. Data were acquired using an LSR II flow cytometer (Becton Dickinson, Franklin Lakes, N.J.) and analyzed with FLOWJO™ software (Tree Star, San Carlos, Calif.).

Phenotypic Analysis of Alloreactive T Cells

The following fluorochrome-labeled monoclonal antibodies were used for cell surface or intra-cellular flow staining of rhesus T cells: CD3 (clone: SP34-2) PerCP-Cy5.5, CD4 (clone: L200) APC-H7, CD28 (clone: CD28.2) APC-H7, CD45RA (clone: 5H9) PE-Cy7, CTLA4 (CD152; clone: BNI3) APC or VB450 (all from BD Biosciences; San Jose, Calif.), CD8 (clone: RPA-T8) AF700, and CD95 (clone: DX2) PE-Cy7 (all from Biolegend; San Diego, Calif.), PD-1(CD279; clone: eBioJ105) PE and Eomesodermin (clone: WD1928) EFLUOR™ 660 (all from eBioscience; San Diego, Calif.). Data were acquired and analyzed as described above. For renal allograft recipients' samples, percentages obtained for specific populations were used to determine absolute numbers based on WBC in the peripheral blood.

Immunofluorescence Staining of Kidney Allografts

Tissues were collected from graft recipients in the control group on the day of euthanasia following clinical evidence of rejection and from those in the DCreg group on POD 28 by open biopsy of the kidney graft. Tissues were embedded in O.C.T. (Miles), snap-frozen and stored at −80° C. Cryostat sections (8-10 μm) were mounted on slides pre-coated with Vectabond (Vector) then fixed in 96% ethanol and allowed to dry. Sections were blocked successively with 5% goat serum and an avidin/biotin blocking kit (Vector). Next, sections were incubated with anti-human CD8 antibody (clone LT8, Abcam, 1:100, overnight, 10° C.), followed by ALEXA FLUOR™ 555-goat anti-mouse IgG (Molecular Probes, 1:100, 1 h, RT). The slides were then blocked with mouse irrelevant IgG1 (BD Biosystems, 1:100, 1 h, RT) and incubated successively with (i) biotin anti-human CTLA4 (CD152) (clone BNI3, BD Biosystems, 1:100, 1 h, RT), (ii) DYLIGHT™ 488-streptavidin (Jackson ImmunoResearch Laboratories, 1:400, 30 minutes, RT), and (iii) ALEXA FLUOR™ 647-conjugated anti-human PD1 (CD279) antibody (clone EH12.2H7, Biolegend, 1:100, 1 hour, RT). Cell nuclei were stained with DAPI (Molecular Probes). Slides were examined with a Nikon Eclipse E800 microscope equipped with a CCD camera (Nikon). At least three different sections per sample were analyzed. Nuclei were stained with DAPI. Slides were examined with a Nikon Eclipse E800 microscope equipped with a CCD camera (Nikon). Leukocyte infiltrates were quantified at 200×, on 3 sections per allograft, with METAMORPH™ Offline 7.7.50n software.

Statistical Analyses

The significance of differences between groups was determined using Kruskal-Wallis one-way analysis of variance or Mann-Whitney U test, as appropriate. Significance was defined as $p<0.05$.

Example 2: Eomesodermin Expression by Alloreactive Non-Human Primate $CD8^+$ Memory T Cells This example describes the finding that donor-specific $Eomes^{lo}CTLA4^{hi}$ $CD8^+$ T memory cells are correlated with prolonged allograft survival.

Figure 1A:
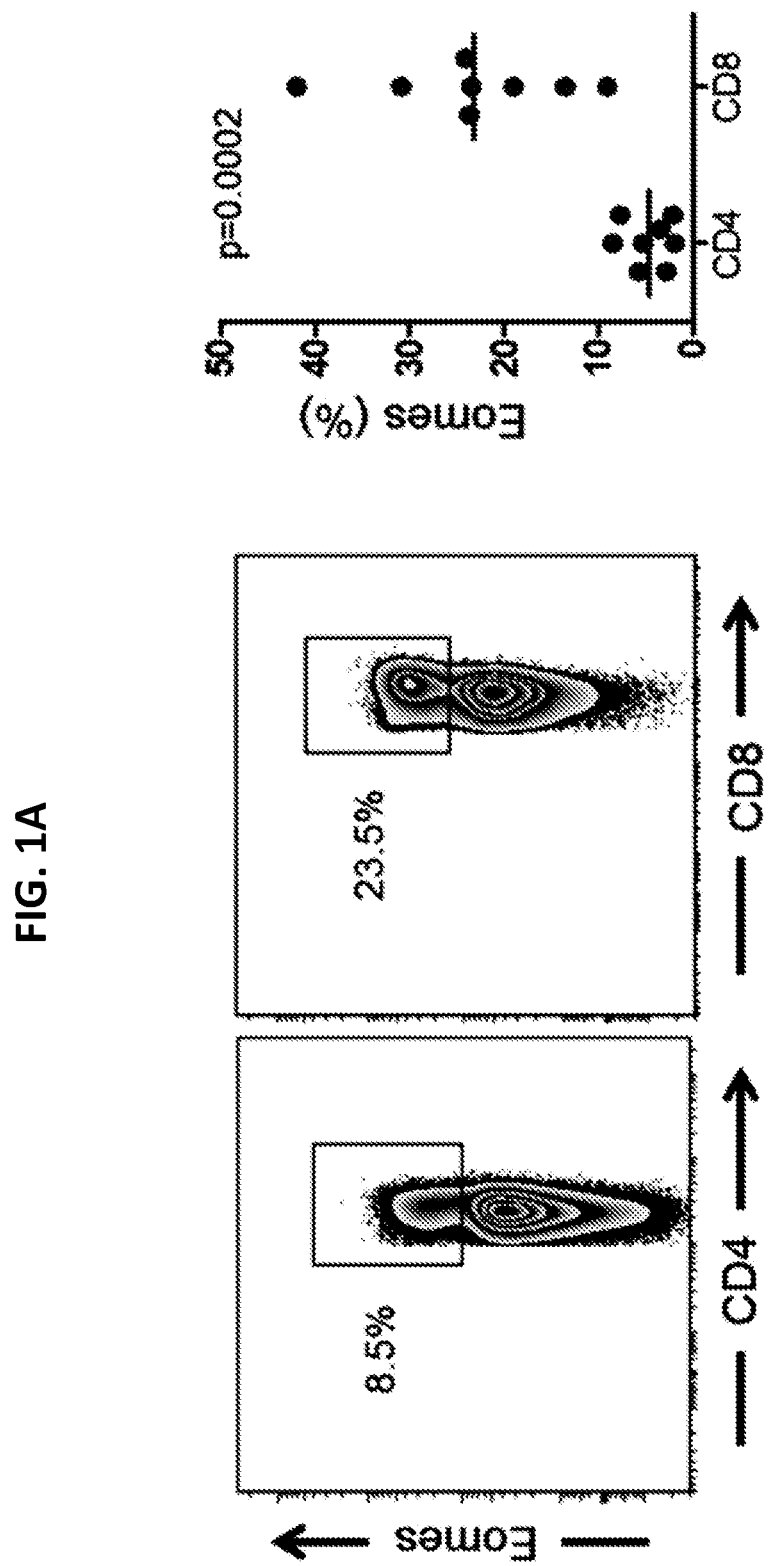
FIGS. 1A-1E: Expression of Eomes by normal monkey naïve and memory $CD4^+$ and $CD8^+$ T cells.
Figure 1B:
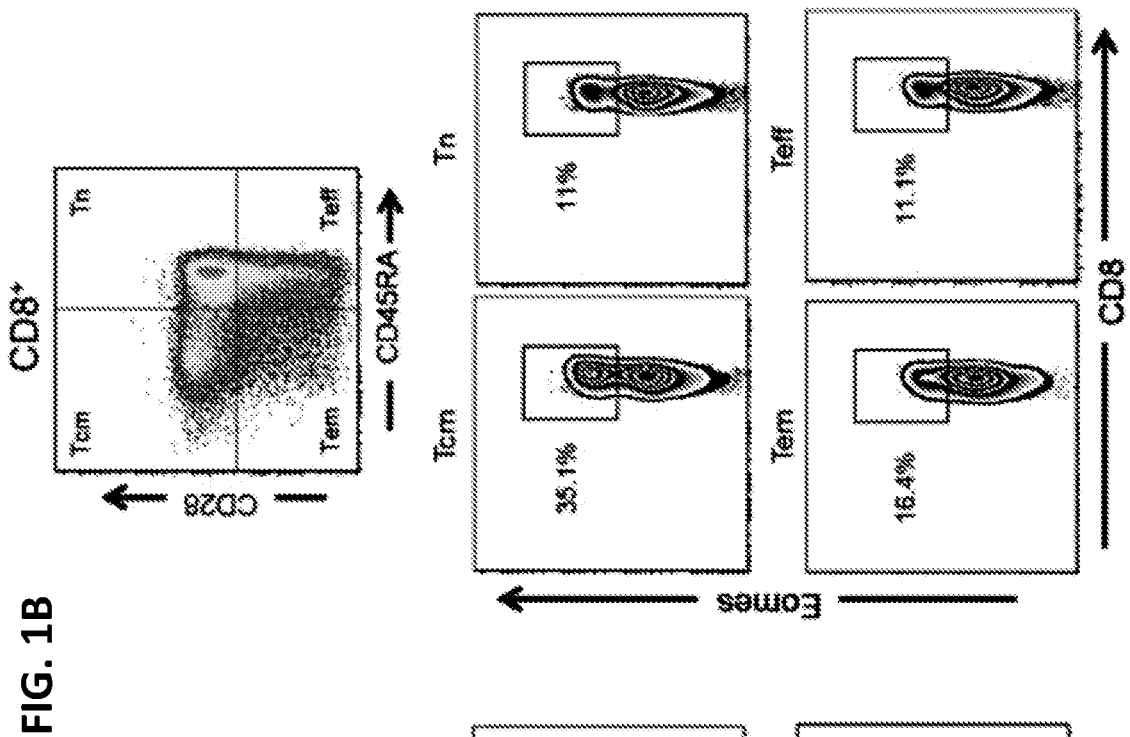
Figure 1B:
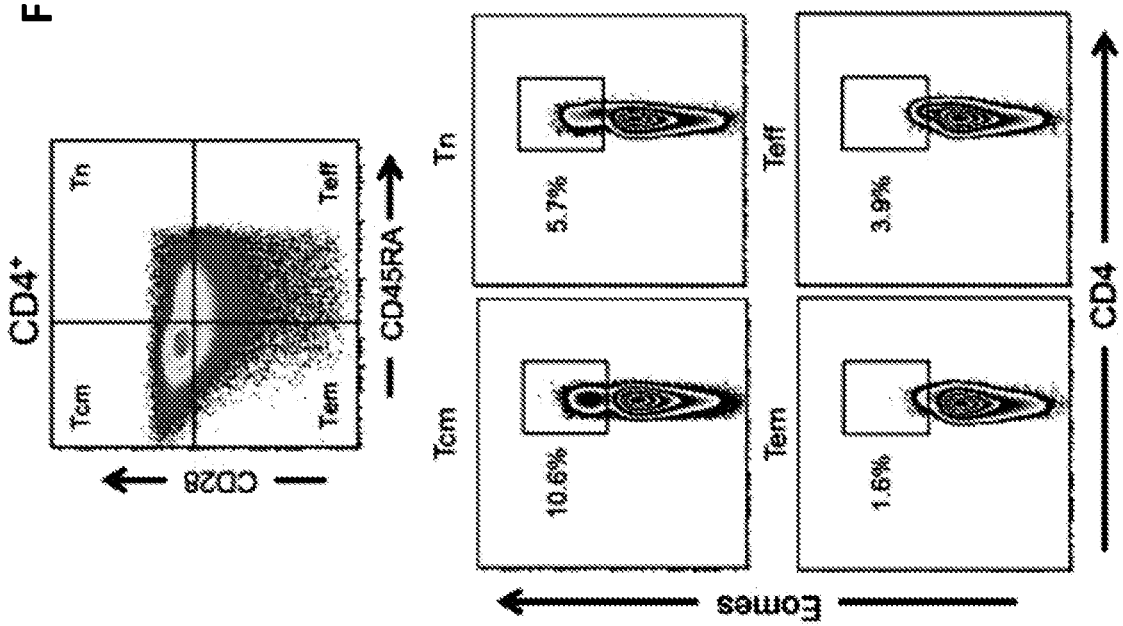
Figure 1C:
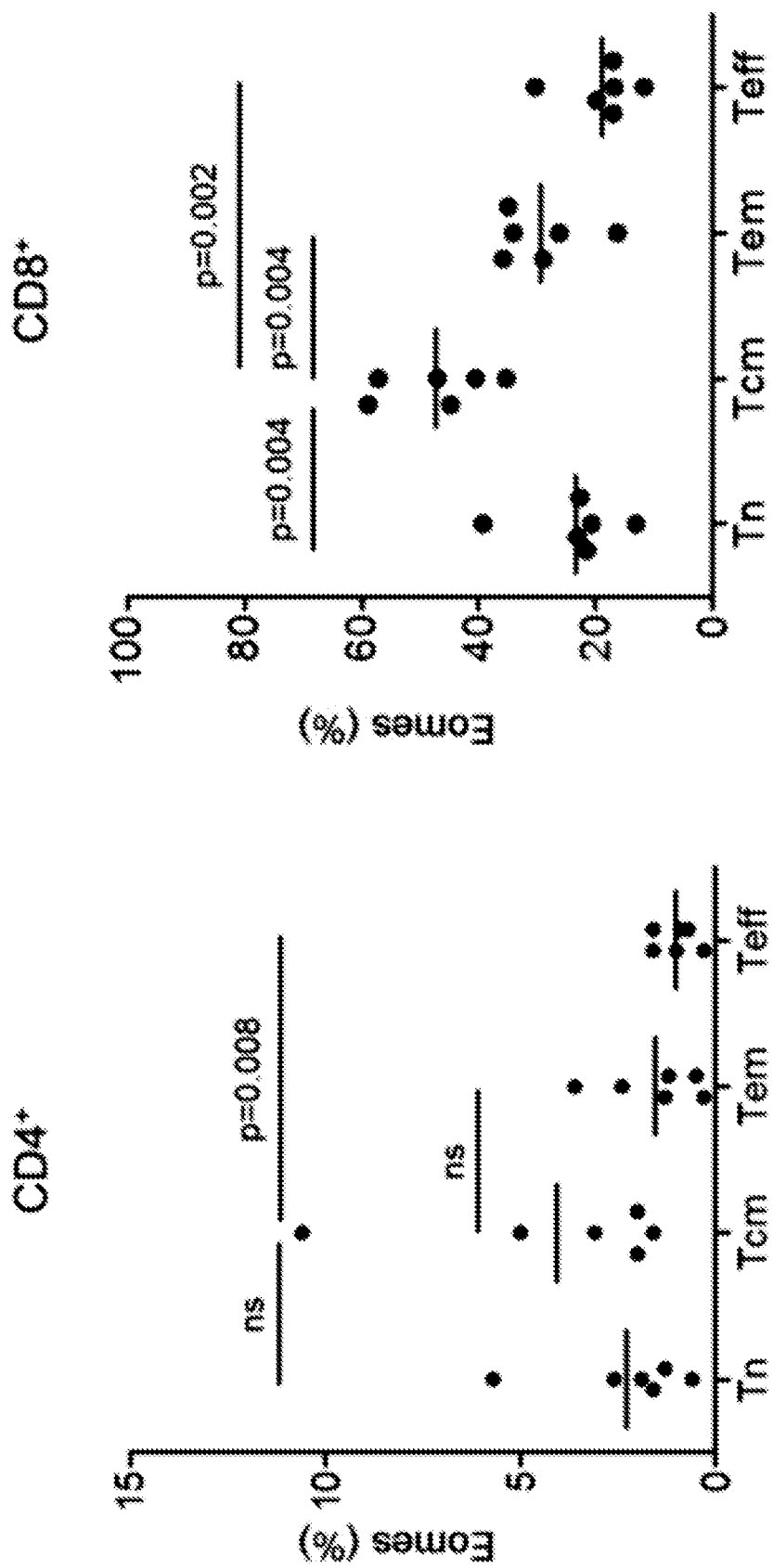

$CD8^+$ Tmem Express High Levels of Eomes Compared to $CD4^+$ Tmem in Normal Rhesus Monkeys Eomes is a T-box transcription factor that plays a key role in the differentiation of Tmem, particularly Tcm (Banerjee et al., *J Immunol* 185(9):4988-4992, 2010). First, the expression of Eomes by normal monkey peripheral blood $CD4^+$ and $CD8^+$ T cells was examined (FIG. 1A). $CD8^+$T cells expressed significantly higher levels (approximately 5-fold) than $CD4^+$T cells. Next, Eomes expression by naïve and memory subsets of $CD4^+$ and $CD8^+$ T cells was evaluated (FIG. 1B), based on their differential expression of CD28 and CD45RA (Pitcher et al., *J Immunol* 168(1):29-43, 2002). Eomes was expressed more strongly by all $CD8^+$ compared to $CD4^+$ naïve and memory T cell subsets. In both $CD4^+$ and especially $CD8^+$ populations, Tcm displayed the highest Eomes expression (FIGS. 1B and 1C). In $CD4^+$T cells, mean Eomes expression by Tcm (4.1%) was significantly higher than that by effector T cells (Teff; 1%), but not naïve (Tn; 2.3%) or effector memory T cells (Tem; 1.6%). In $CD8^+$ T cells, mean Eomes expression by Tcm (47.3%) was significantly higher than for all other subsets—Tem (29.4%), Tn (23.5%) and Teff (18.9%) (FIG. 1C).

Figure 1D:
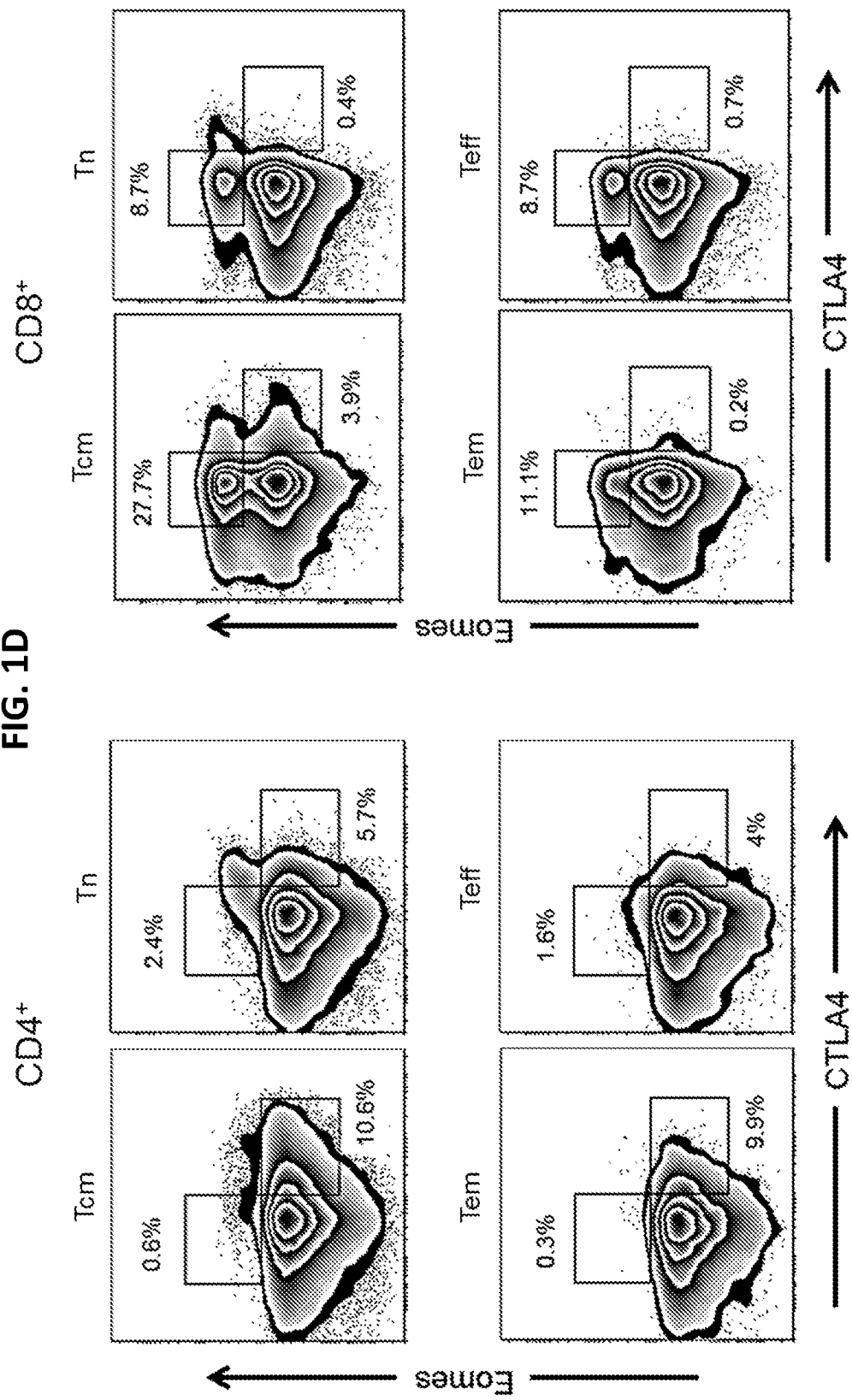

Eomes versus CTLA4 expression by both $CD4^+$ and $CD8^+$ naïve and Tmem subsets was then evaluated (FIG. 1D). In correlation with previous results, low percentages of $Eomes^{hi}CTLA4^{lo}$ and high percentages of $Eomes^{lo}CTLA4^{hi}$ cells were detected in all $CD4^+$ T cell subsets, compared to $CD8^+$ T cells. $CD4^+$Tcm and $CD4^+$Tem showed higher frequencies of $Eomes^{lo}CTLA4^{hi}$ cells. Although $CD8^+$ T cell subsets exhibited minimal percentages of $Eomes^{lo}CTLA4^{hi}$ cells (<4%), $CD8^+$Tcm comprised the highest percentage of $Eomes^{lo}CTLA4^{hi}$ cells.

Figure 1E:
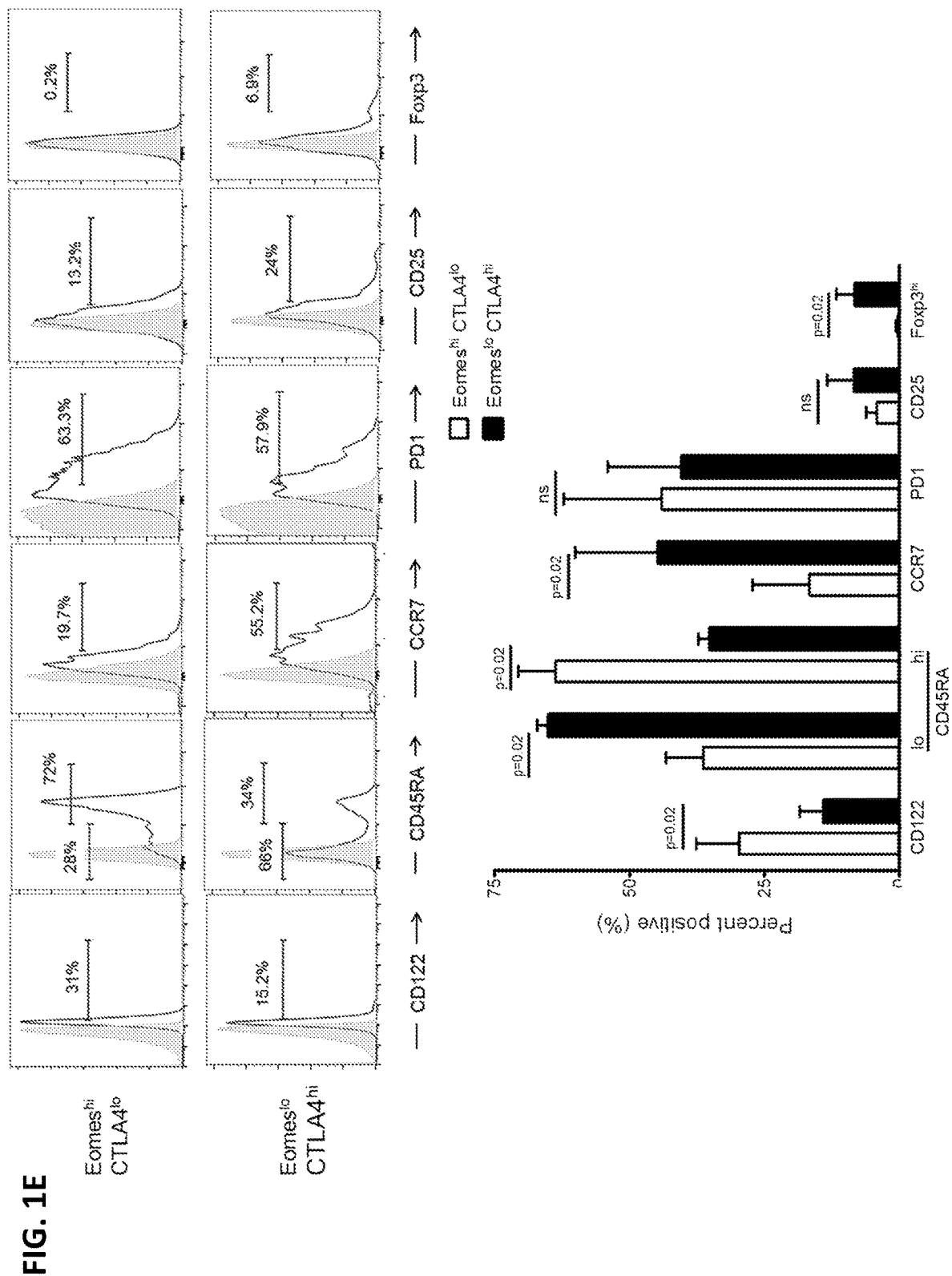

$Eomes^{lo}CTLA4^{hi}CD8^+$ T Cells Include a Higher Proportion of Putative Regulatory Cells In humans and rodents, memory-like regulatory $CD8^+$ T cells suppress both autoimmune and alloimmune responses (Smith and Kumar, *Trends Immunol* 29:337-342, 2008; Guillonneau et al., *Curr Opin Organ Transplant* 15:751-756, 2010; Li et al., *Cell Mol Immunol* 11:326-331, 2014). $CD8^+CD122(IL-2R\beta$ $chain)^+PD1^+$ T cells suppress T-cell proliferation and inflammatory cytokine production (Dai et al., *J Immunol* 185:803-807, 2010), inhibit allograft rejection (Wan et al., *J Immunol* 180:113-121, 2008; Dai et al., *Am J Transplant* 14:39-48, 2014) and mediate allograft acceptance (Krupnick et al., *J Clin Invest* 124:1130-1143, 2014). Expression of CD122, CD45RA, CCR7, PD1, CD25 and Foxp3 by $Eomes^{lo}CTLA4^{hi}$ versus $Eomes^{hi}CTLA4^{lo}CD8^+$ T cells was evaluated in naïve monkeys (FIG. 1E). The incidence of $CD122^+$ cells was higher in the $Eomes^{hi}CTLA4^{lo}$ compared to the $Eomes^{lo}CTLA4^{hi}$ population. Overall, the $Eomes^{lo}CTLA4^{hi}$ population exhibited a more central memory phenotype; that is, a significantly higher incidence of CCR7 and a lower incidence of $CD45RA^+$ cells than the $Eomes^{hi}CTLA4^{lo}$ population. CD25 expression was low on both populations, but higher on $Eomes^{lo}CTLA4^{hi}$ cells. Furthermore, the $Eomes^{lo}CTLA4^{hi}CD8^+$ population exhibited a higher incidence of $Foxp3^+$ cells compared to $Eomes^{lo}CTLA4^{lo}CD8^+$ T cells. These findings indicate that low Eomes and high CTLA4 expression by rhesus $CD8^+$ T cells is associated with a subset of cells with a regulatory phenotype.

$CD8^+$ Tmem Express Minimal CTLA4 Compared to $CD4^+$ Tmem in Normal Rhesus Monkeys There is recent evidence (Hegel et al., *Eur J Immunol* 39(3):883-893, 2009) that co-inhibitory CTLA4 (CD152) may selectively inhibit Eomes expression by rodent $CD8^+$ T cells. Systemic administration of DCreg one week before transplantation, together with CTLA4Ig is associated with upregulation CTLA4 and PD1 by donor-reactive Tmem (Ezzelarab et al., *Am J Transplant* 13(8):1989-2005, 2013). It was therefore hypothesized that high levels of CTLA4 might be associated with low levels of Eomes expression by Tmem after transplantation in CTLA4Ig-treated recipient monkeys.

Figure 2A:
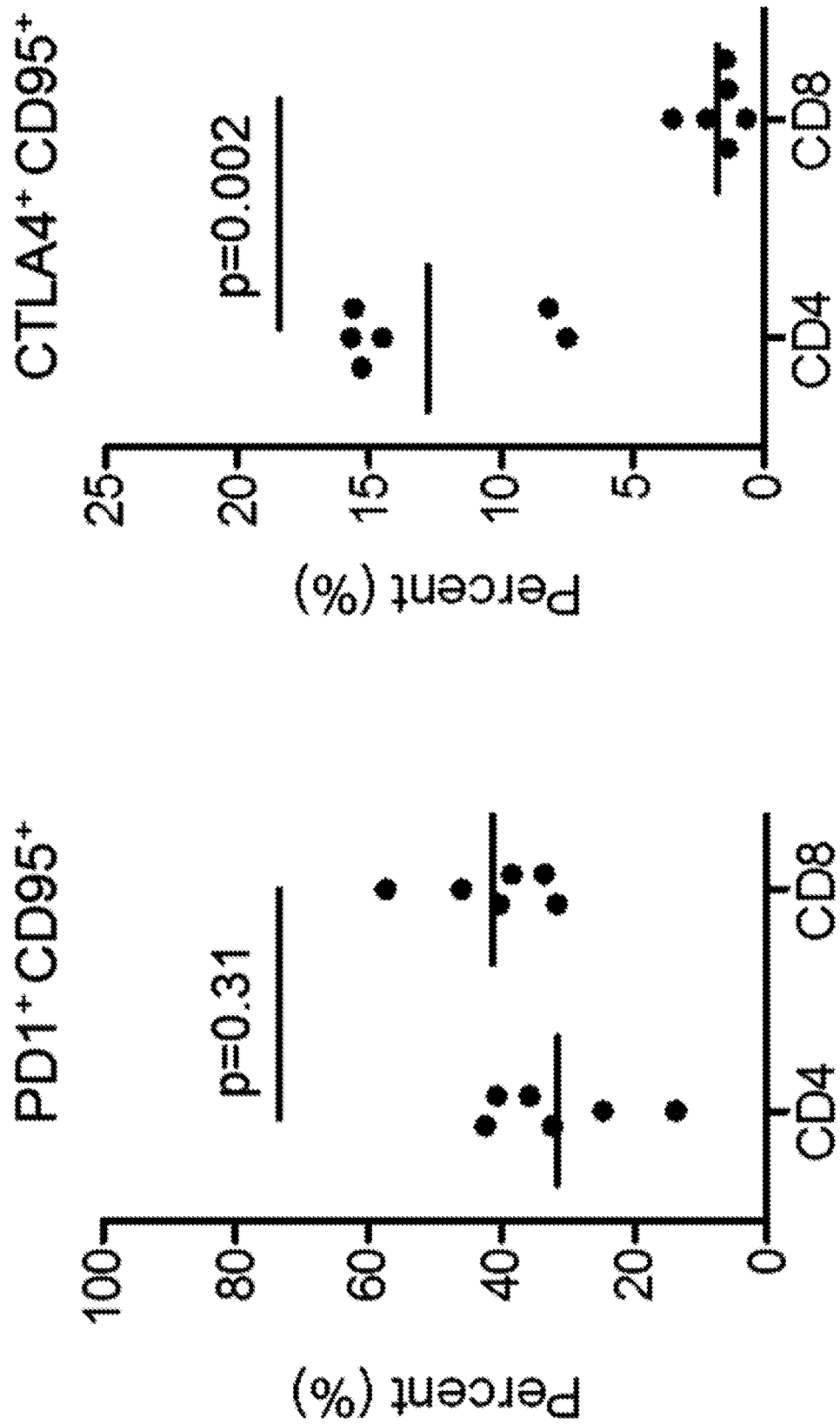

The next study evaluated CTLA4 and PD1 expression by normal monkey Tmem and alloreactive T cells in the presence or absence of CTLA4Ig. In rhesus macaques, including transplant recipients (Kean et al., *Am J Transplant* 7(2):320-335, 2007; Larsen et al., *Am J Transplant* 10(11):2396-2409, 2010; Page et al., *Am J Transplant* 12(1):115-125, 2012), CD95 expression is used to identify Tmem (Pitcher et al., *J Immunol* 168(1):29-43, 2002). In normal animals (FIG. 2A), the frequency of PD1$^+$CD95$^+$ Tmem was comparable between the CD4$^+$ and CD8$^+$ T cell populations. In contrast, the frequency of CTLA4$^+$CD95$^+$ Tmem was significantly lower in the quiescent CD8$^+$ T cell population.

Figure 2C:
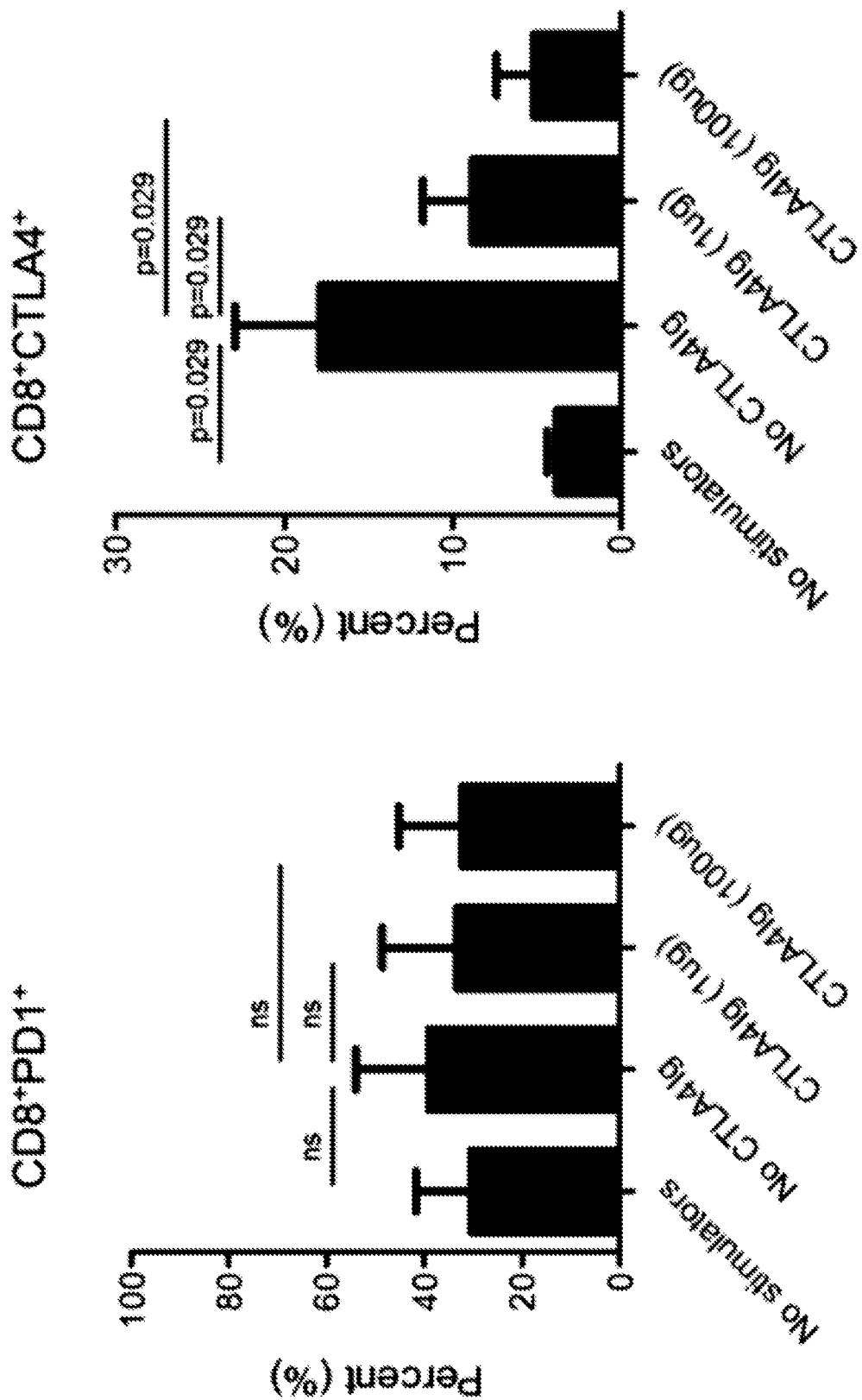
Figure 9:
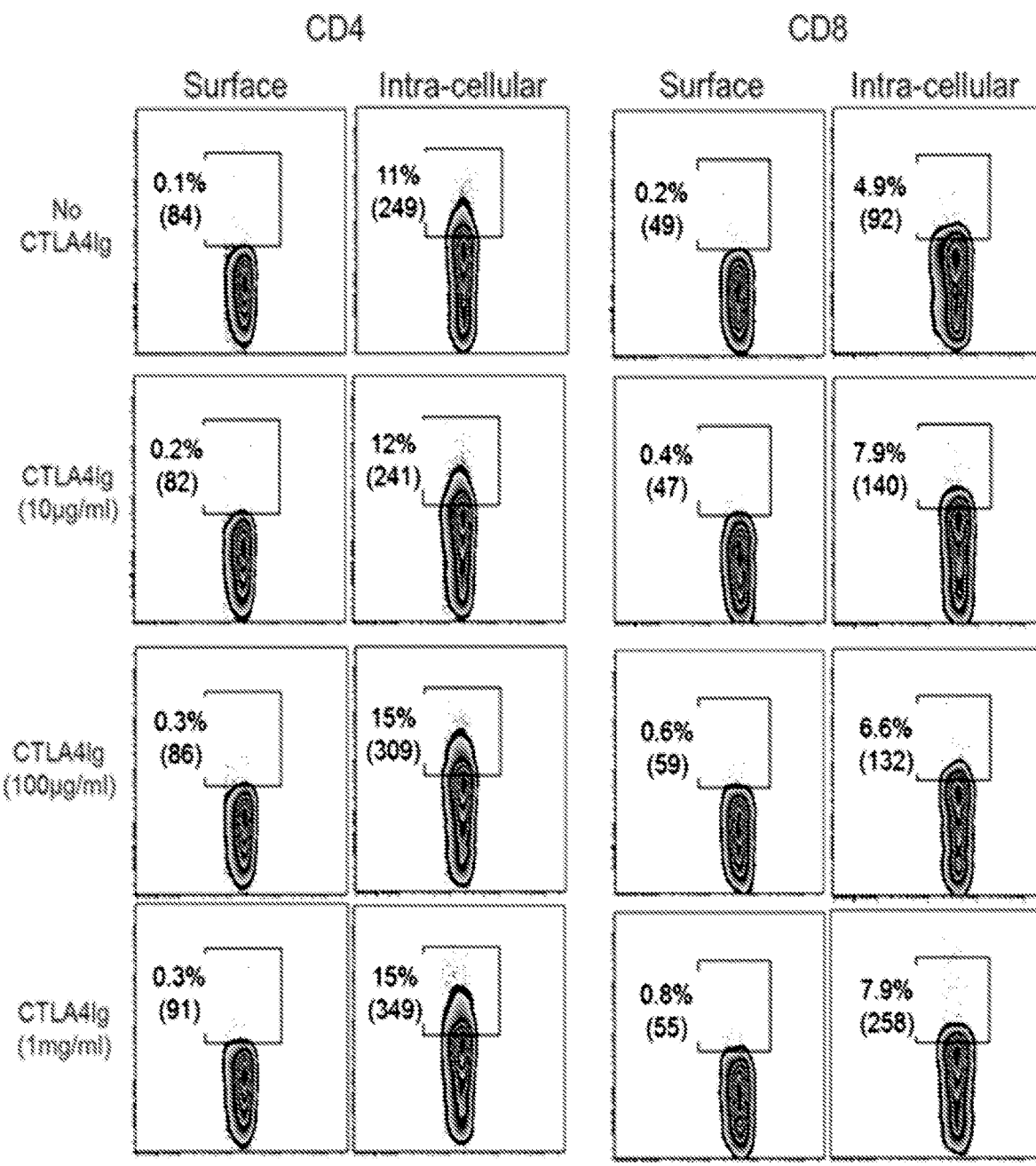
FIG. 9: Addition of CTLA4Ig to cultures does not interfere with subsequent CTLA4 staining. Addition of CTLA4Ig (1-100 µg/ml) at the start of 5-day rhesus monkey PBMC cultures does not interfere with subsequent staining of extensively-washed T cells for surface and intracellular CTLA4 expression (as described in Example 1) at the end of the culture period.

CD28 CB with CTLA4Ig Significantly Reduces CTLA4 Expression by CD8$^+$ T Cells after Allostimulation While the co-inhibitory molecules CTLA4 and PD1 are considered markers of T cell exhaustion and regulation, they are also expressed by activated T cells (Vibhakar et al., *Exp Cell Res* 232(1):25-28, 1997; Linsley et al., *Immunity* 4(6):535-543, 1996). The influence of CD28 CB with CTLA4Ig on CTLA4 and PD1 expression by alloreactive CD8$^+$ T cells was tested following their stimulation in MLR. In the absence of CTLA4Ig, mean CTLA4 expression by CD8$^+$ T cells was upregulated almost 5-fold. Expression of PD1 was slightly increased although not significantly (FIGS. 2B and 2C). Meanwhile, reduced CD8$^+$ T cell proliferation in the presence in CTLA4Ig was accompanied by a significant reduction in CTLA4$^+$ cells, in a CTLA4Ig concentration-dependent manner, while no similar reduction was observed for PD1$^+$ cells (FIGS. 2B and 2C). Notably, no evidence was found that, under these experimental conditions, anti-CTLA4 mAb used to stain CTLA4 bound to any residual cell-bound fusion protein with consequent 'artificial' reduction in CTLA4 staining (FIG. 9).

Figure 3A:
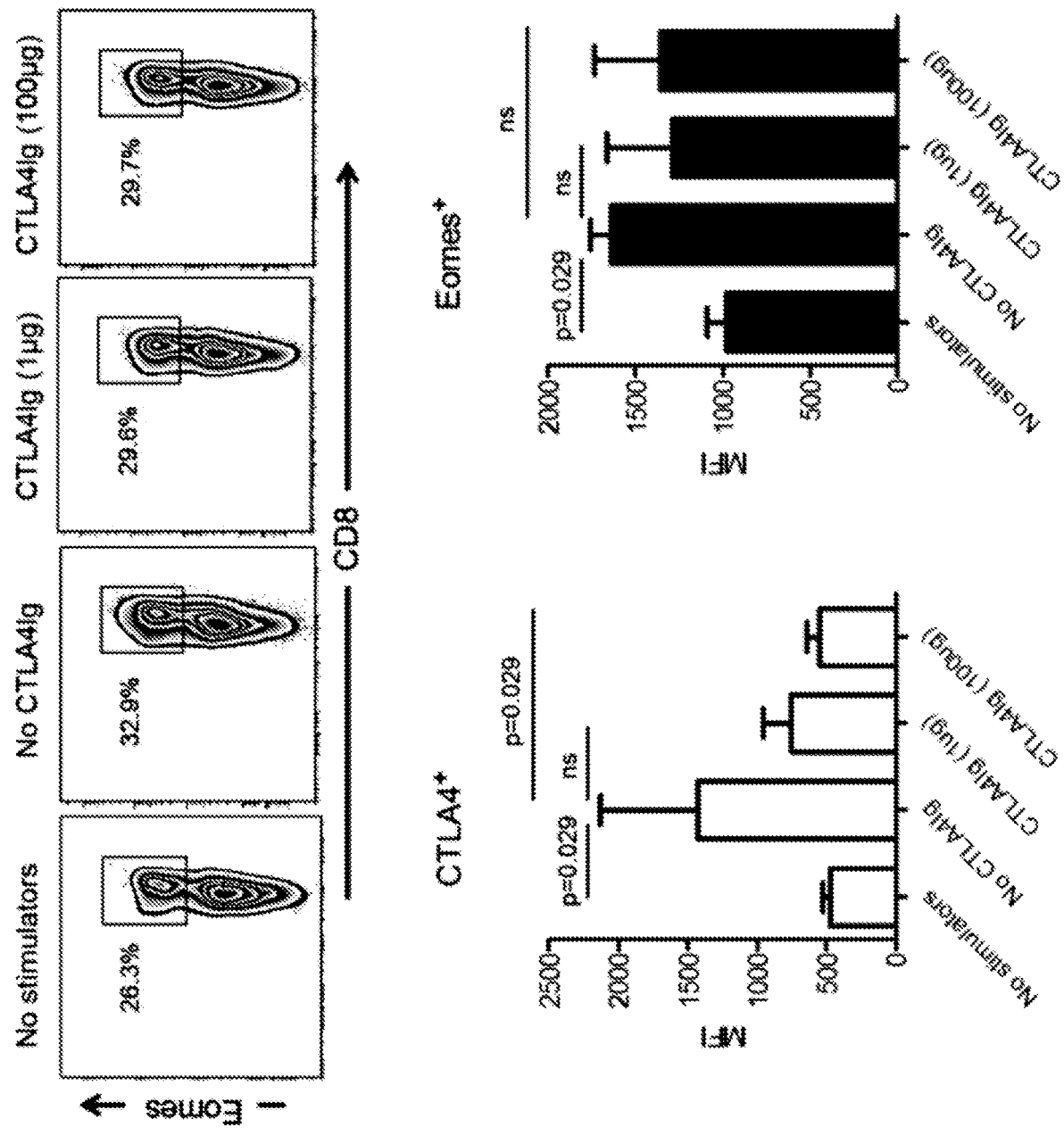
FIGS. 3A-3B: CD28 co-stimulation blockade does not reduce Eomes expression compared to CTLA4 expression by allostimulated normal monkey CD8+ T cells.

CD28 CB with CTLA4Ig Does Not Affect Eomes Expression by CD8$^+$ T Cells after Allostimulation Having shown that CD28 CB reduces proliferating alloreactive CD8$^+$CTLA4$^{hi}$ T cells (FIG. 2B), the influence of CTLA4Ig on Eomes expression by CD8$^+$ T cells following allostimulation was next examined Expression of Eomes was increased significantly following allostimulation, but was not reduced by addition of CTLA4Ig at the start of MLR cultures. At the same time, however, CTLA4 expression was reduced significantly (FIG. 3A).

Figure 3B:
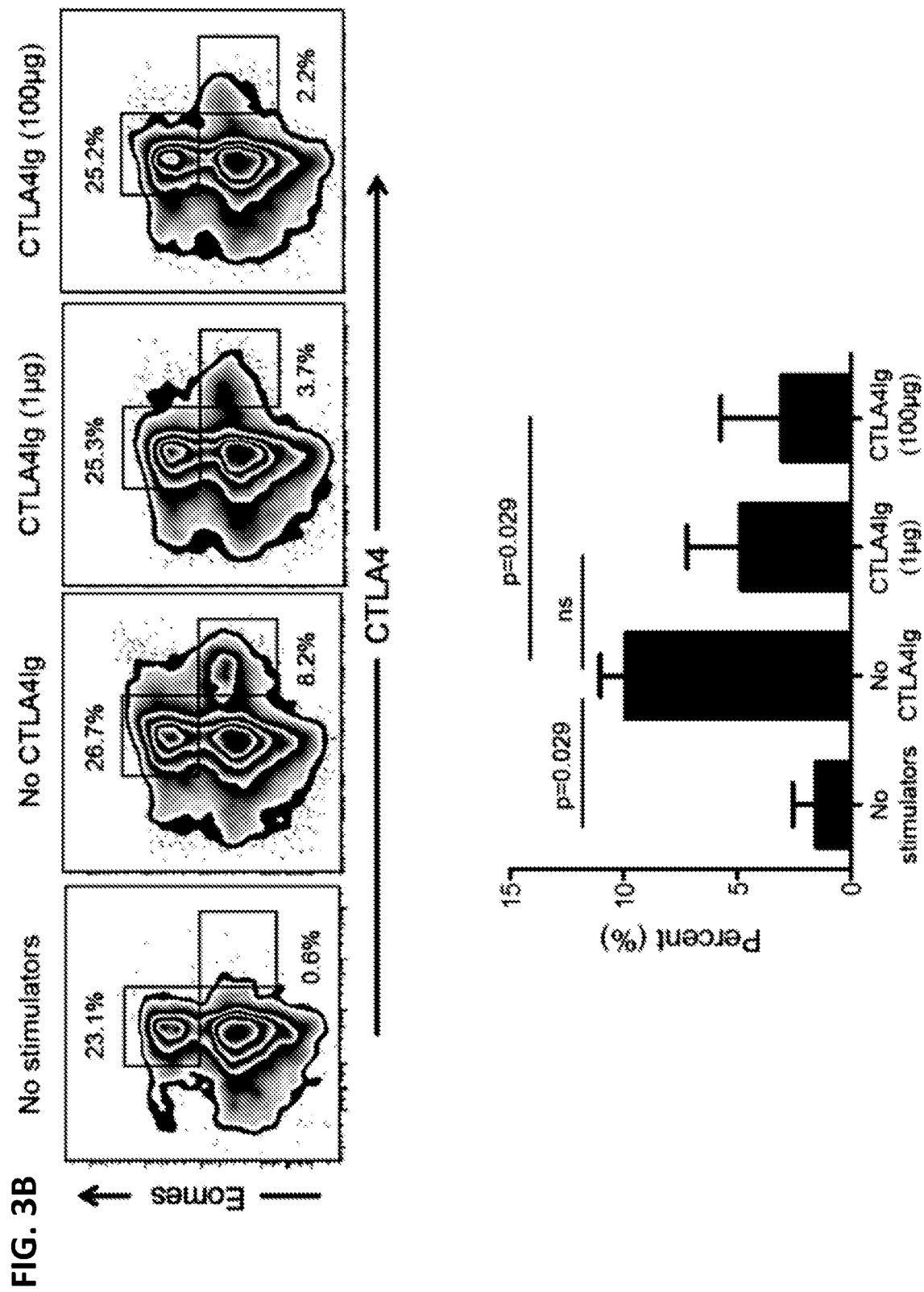

In correlation, no marked changes in the incidence of Eomes$^{hi}$CTLA4$^{lo}$CD8$^+$T cells were observed after allostimulation in the absence or presence of CTLA4Ig (FIG. 3B, upper panel), while the incidence of Eomes$^{lo}$CTLA4$^{hi}$CD8$^+$T cells was reduced markedly by CTLA4Ig, in a concentration-dependent manner (FIG. 3B, lower panel).

Figure 4A:
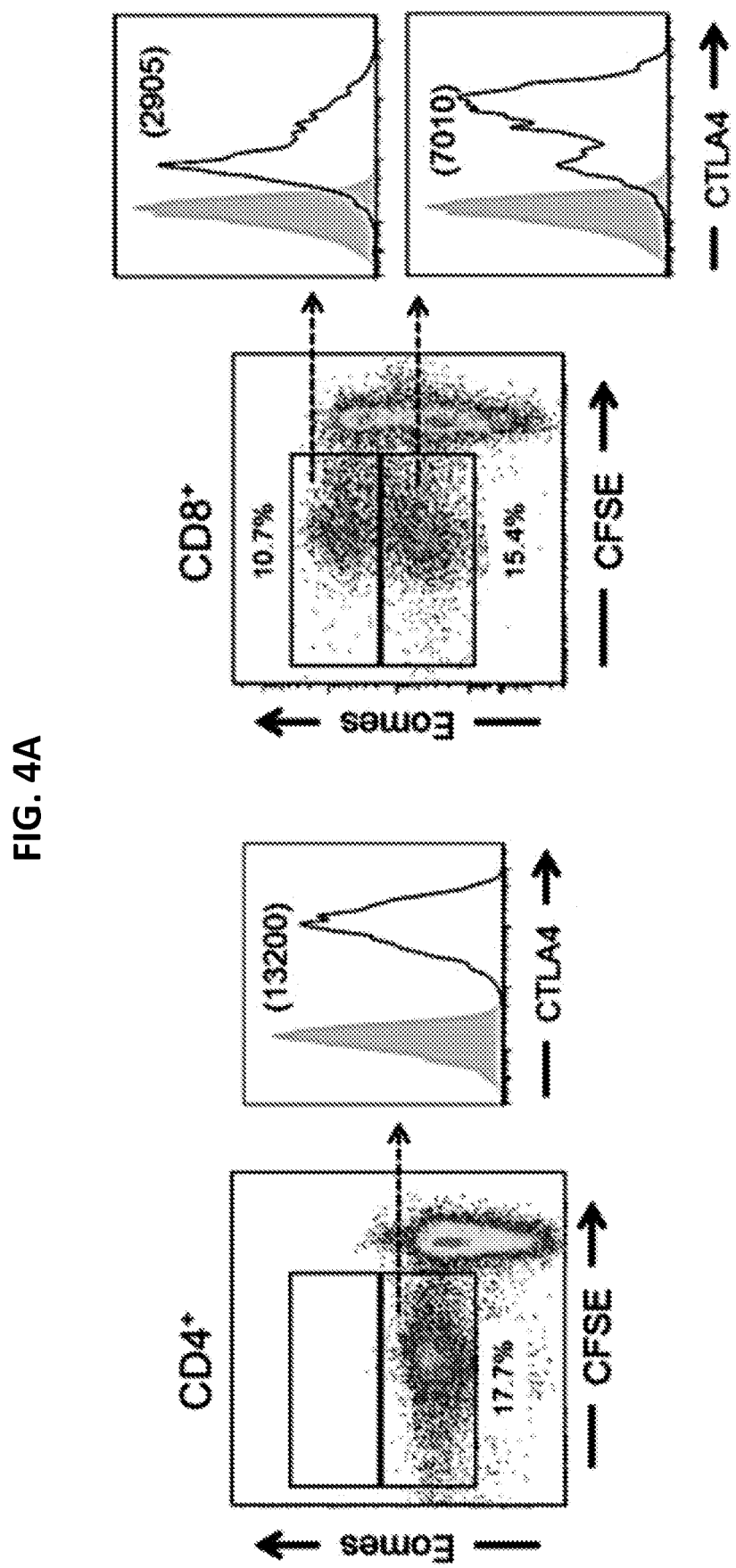
FIGS. 4A-4B: Two distinct populations of $Eomes^{hi}$ and $Eomes^{lo}$ proliferating CD8+ T cells are observed following allostimulation of normal monkey T cells.
Figure 4B:
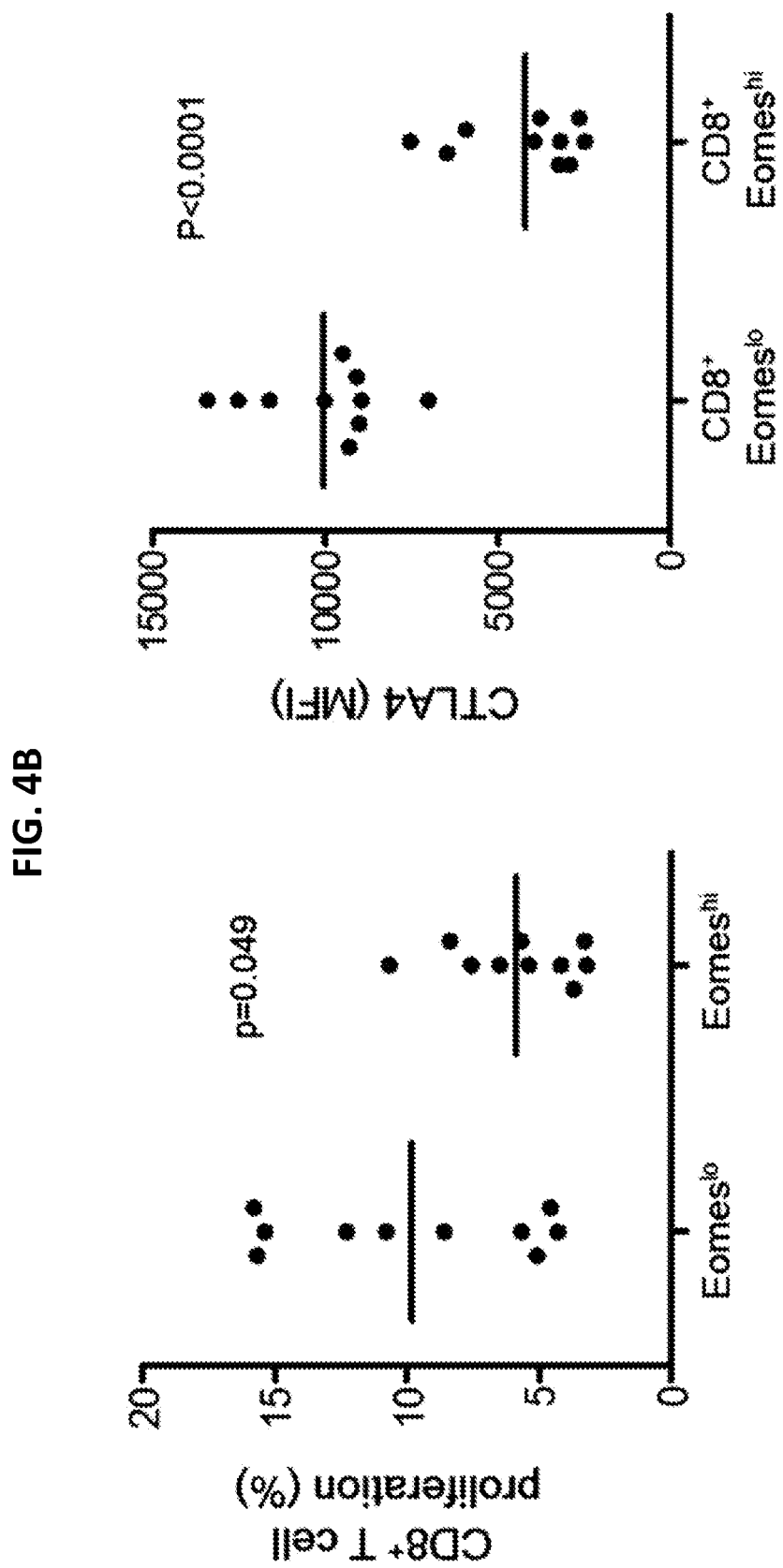

Reciprocal Relationship Between Eomes and CTLA4 Expression by Alloreactive T Cells It was hypothesized that an inverse correlation might exist between CTLA4 and Eomes expression by alloactivated rhesus Tmem. In normal monkeys, proliferating alloreactive T cells upregulate CTLA4 (FIG. 2B). All proliferating CD4$^+$T cells displayed low Eomes expression, whereas proliferating CD8$^+$T cells displayed two distinct populations, with either low or high Eomes expression. Proliferation of CD8$^+$T cells with low Eomes expression was significantly higher than that of those with high Eomes expression (FIGS. 4A and 4B). CTLA4 expression by proliferating CD4$^+$ and CD8$^+$ T cells was also examined Proliferating CD4$^+$T cells (Eomes$^{lo}$) displayed higher levels of CTLA4 than proliferating Eomes$^{lo}$ and Eomes$^{hi}$ CD8$^+$ T cells (FIG. 4A). CD8$^+$Eomes$^{lo}$T cells expressed significantly higher levels of CTLA4 than CD8$^+$Eomes$^{hi}$ T cells (FIG. 4B, right panel). These data indicate that upregulation of CTLA4 is associated with reduced Eomes expression by alloreactive CD4$^+$ and CD8$^+$ T cells.

Figure 5A:
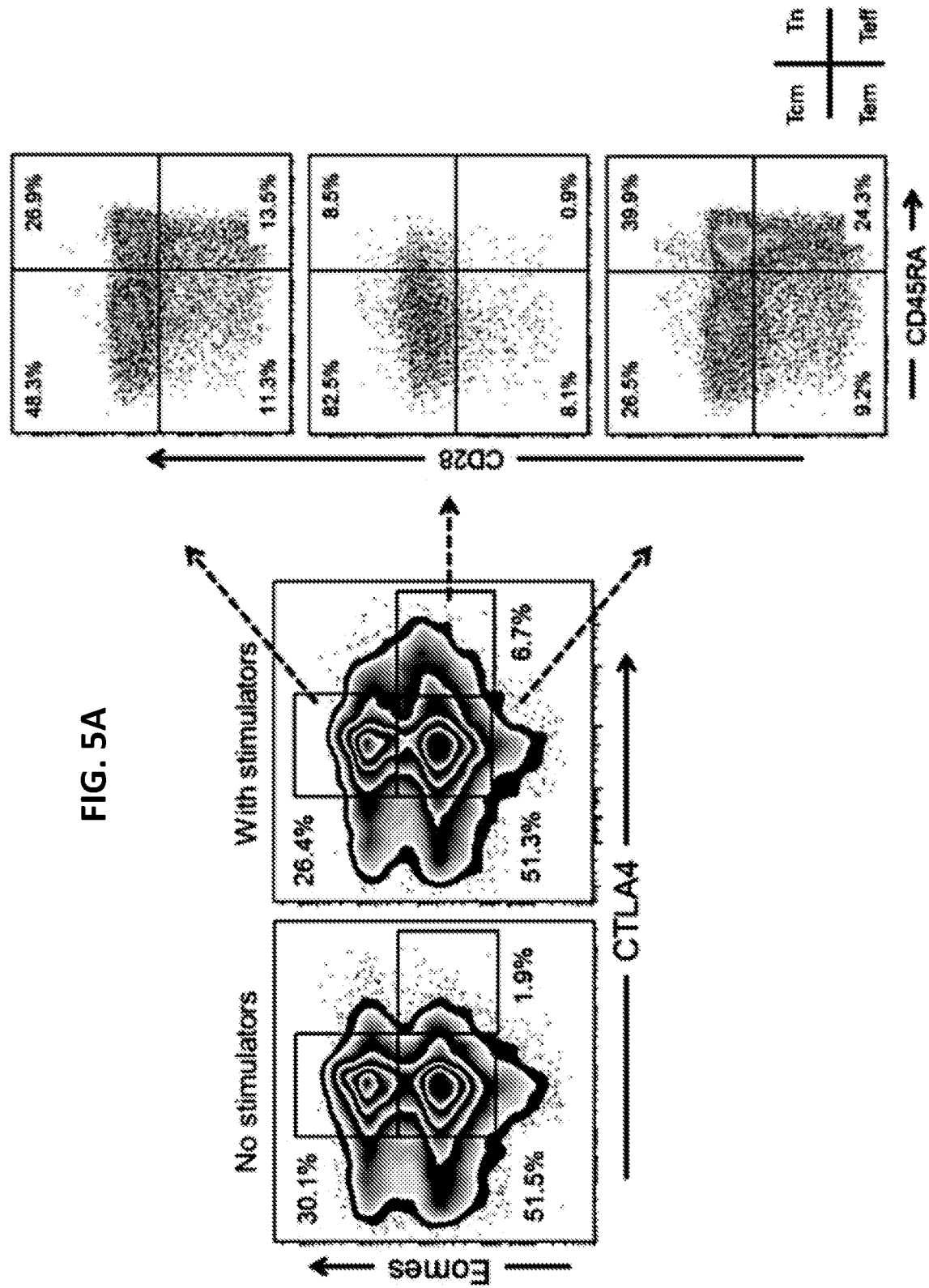
FIGS. 5A-5B: Increased frequency of central memory T cells in $Eomes^{lo}CTLA4^{hi}$ CD8+ T cell population following allostimulation.
Figure 5B:
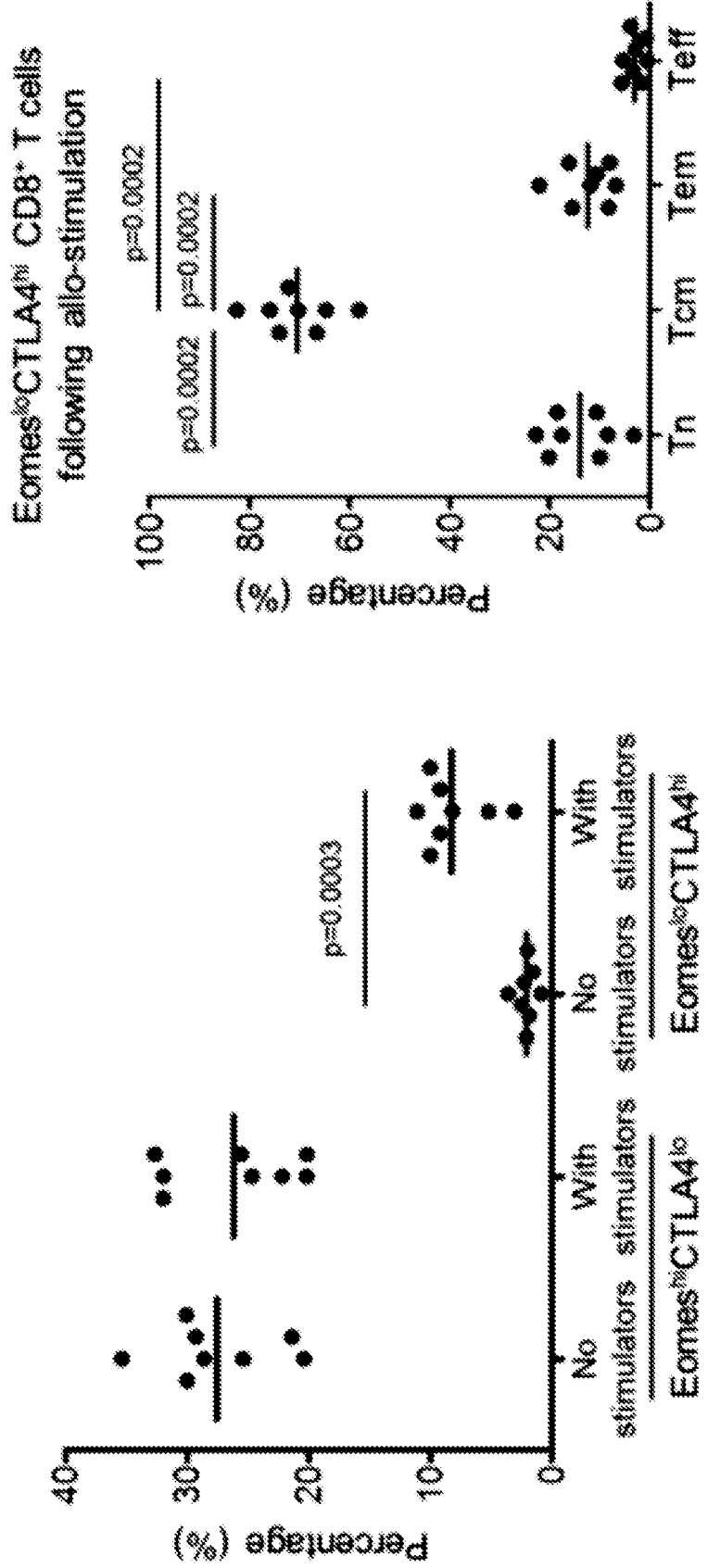

Alloreactive Eomes$^{lo}$CTLA4$^{hi}$CD8$^+$ T Cells Comprise an Increased Incidence of Tcm The memory phenotype of Eomes$^{lo}$ and Eomesh$^{hi}$CD8$^+$ T cells following allostimulation was next evaluated. When cultured without stimulation, CD8$^+$ T cells comprised a much higher proportion of Eomes$^{hi}$CTLA4$^{lo}$ than Eomes$^{lo}$CTLA4$^{hi}$T cells. As in the previous experiment, no significant changes were observed in the percentages of Eomes$^{hi}$CTLA4$^{lo}$ or Eomes$^{lo}$CTLA4$^{lo}$ T cells following allostimulation; however, Eomes$^{lo}$CTLA4$^{hi}$T cells increased significantly (FIGS. 5A left and 5B left). Next, naïve and memory T cell subsets among Eomes$^{lo}$CTLA4$^{hi}$CD8$^+$ T cells were examined (FIG. 5A, right). Compared with Eomes$^{hi}$CTLA4$^{lo}$ or the Eomes$^{lo}$CTLA4$^{lo}$ T cells, Tcm in the Eomes$^{lo}$CTLA4$^{hi}$CD8$^+$ population were markedly enriched, compared to Tn, Tem or Teff (FIG. 5B, right).

Figure 6:
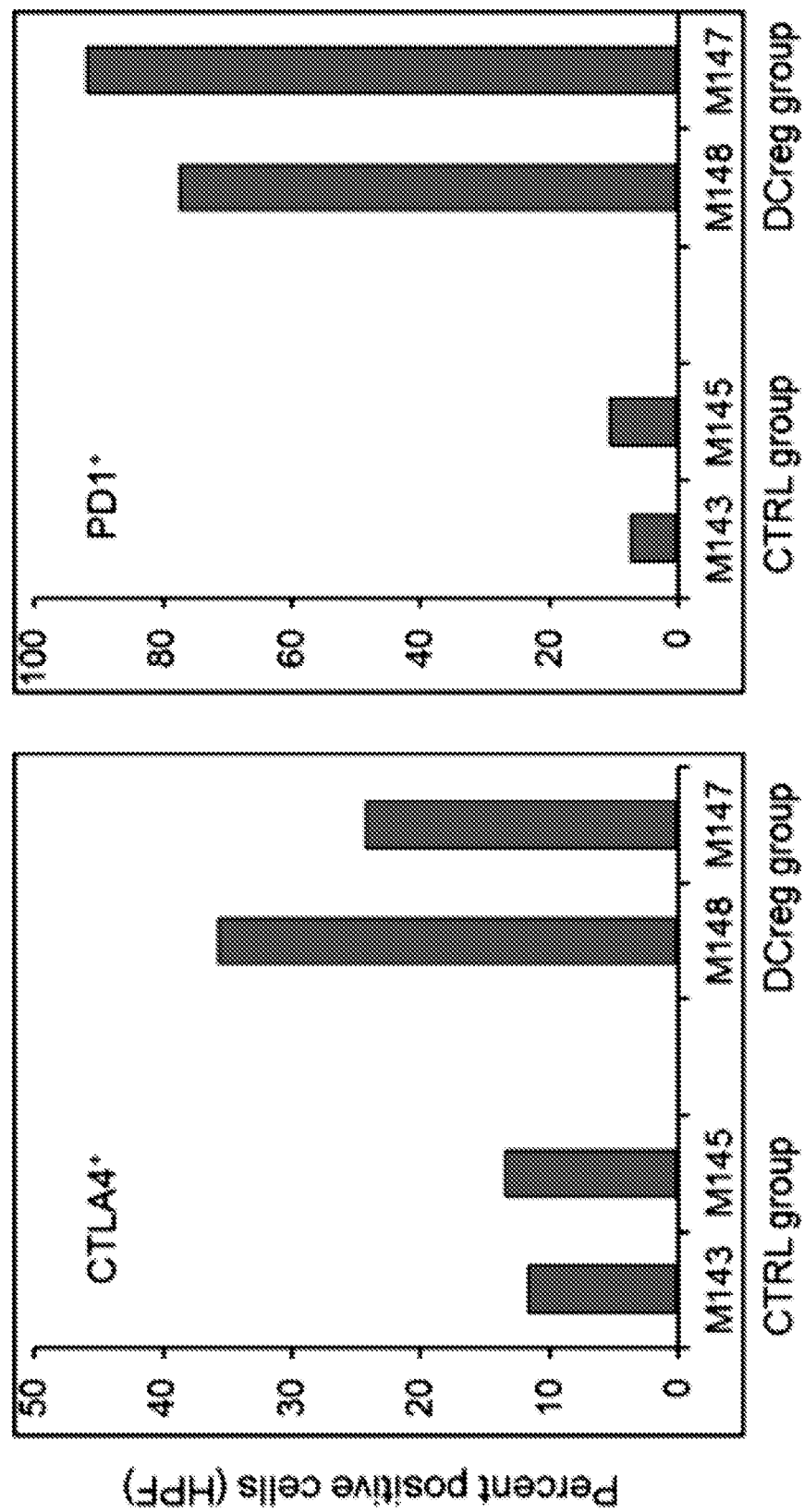
FIG. 6: CTLA4 and PD1 expression by graft-infiltrating CD8+T cells in rhesus monkey kidney transplant recipients. CTLA4 (CD152) and PD1 (CD279) expression by CD8+ T cells in renal allografts was examined by immunofluorescence staining. Nuclei were stained with DAPI. Slides were examined with a Nikon Eclipse E800 microscope equipped with a CCD camera (Nikon). Leukocyte infiltrates were quantified at 200×, on 3 sections per allograft, with META-MORPH™ Offline 7.7.50n software. Numbers of CTLA4+ and PD1+CD8+ T cells per high power field (HPF) in the allograft tissue of the control and DCreg-treated monkeys are shown.

CTLA4 and PD1 Expression by CD8$^+$ T Cells in Renal Allografts One Month after Transplantation In a previous study, rhesus renal allograft recipients given DCreg infusion and exhibiting prolonged graft survival displayed upregulation of co-inhibitory CTLA4 and PD1 by circulating CD8$^+$Tmem in response to ex vivo donor but not 3$^{rd}$ party stimulation (Ezzelarab et al., *Am J Transplant* 13(8):1989-2005, 2013). It was hypothesized that a similar profile of donor-reactive T cells might be observed in the grafts of these DCreg recipients. Thus, CTLA4 and PD1 expression by graft-infiltrating CD8$^+$ T cells was examined and quantified one month post-transplant in two recipients from each of the control and DCreg groups (FIG. 6). In the control group, graft-infiltrating CD8$^+$ T cells showed minimal CTLA4 and PD1 expression, whereas strong expression of CTLA4 and PD1 by CD8$^+$ T cells was observed in renal allografts of the DCreg group. This was consistent with the corresponding upregulation of these inhibitory molecules on host CD8$^+$ T cells following ex vivo stimulation with donor Ag at the same time post-transplant (Ezzelarab et al., *Am J Transplant* 13(8):1989-2005, 2013).

Figure 7A:
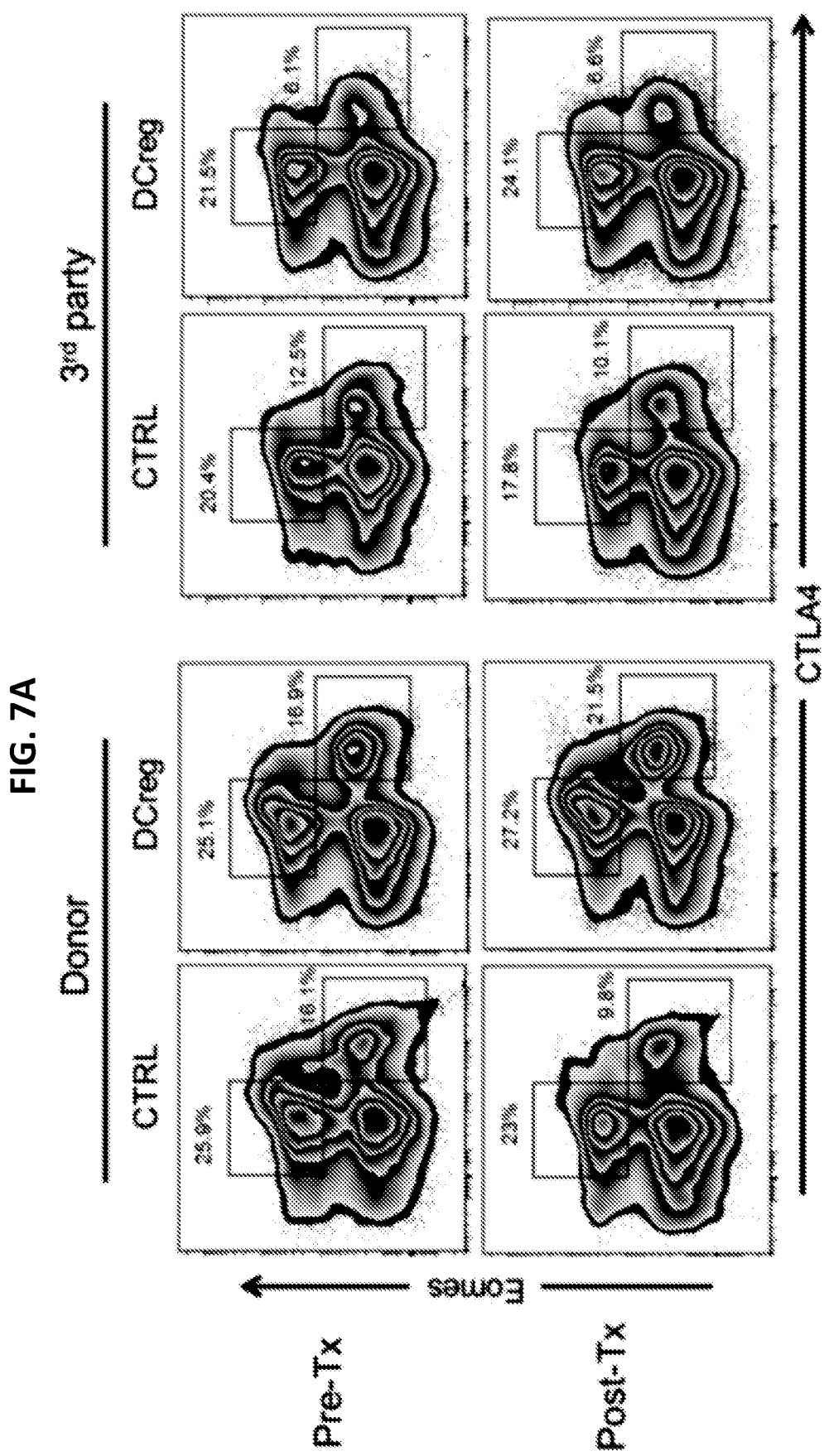
FIGS. 7A-7B: DCreg infusion spares reductions in donor-specific $Eomes^{lo}CTLA4^{hi}$ CD8+Tcm in CTLA4Ig-treated renal allograft recipients.
Figure 7B:
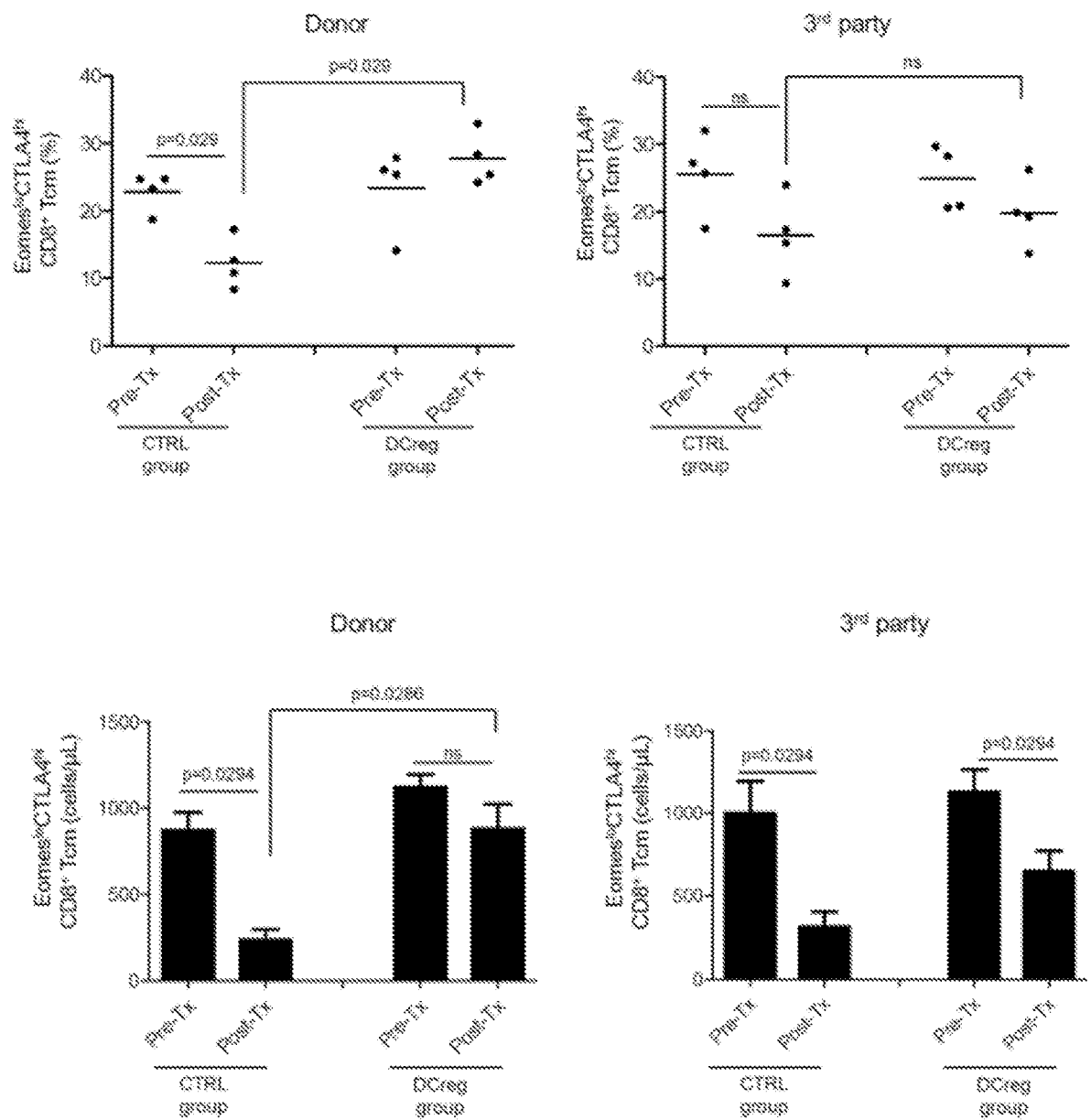

DCreg Infusion Promotes Donor-Specific Eomes$^{lo}$CTLA4$^{hi}$ CD8$^+$ Tcm in CTLA4g-Treated Renal Allograft Recipients Next, the relevance of these findings to our transplant model (FIG. 7A), in which DCreg infusion in CTLA4Ig-treated recipients was associated with attenuation of anti-donor Tmem responses, was tested (Ezzelarab et al., *Am J Transplant* 13(8):1989-2005, 2013). The percentages (FIG. 7B; top panels) and absolute numbers (FIG. 7B; bottom panels) of peripheral blood alloreactive Eomes$^{lo}$CTLA4$^{hi}$ CD8$^+$ Tcm in renal allograft recipients following donor or 3$^{rd}$ party stimulation was examined, before and 1-2 months post-transplant, with or without DCreg infusion. In control animals (no DCreg infusion), donor-reactive Eomes$^{lo}$CTLA4$^{hi}$ CD8$^+$ Tcm were reduced significantly after transplantation compared to before transplantation (FIG. 7B). By contrast, in graft recipients given DCreg infusion, the frequency of Eomes$^{lo}$CTLA4$^{hi}$ CD8$^+$ Tcm following donor stimulation was increased modestly post-transplant compared to before transplantation (FIG. 7B). More importantly, the mean percentage and absolute numbers of Eomes$^{lo}$CTLA4$^{hi}$ CD8$^+$ Tcm in the DCreg group was significantly higher than that in the control group post-transplant. No similar differences were observed in response to 3$^{rd}$ party stimulation in either group.

Figure 8:
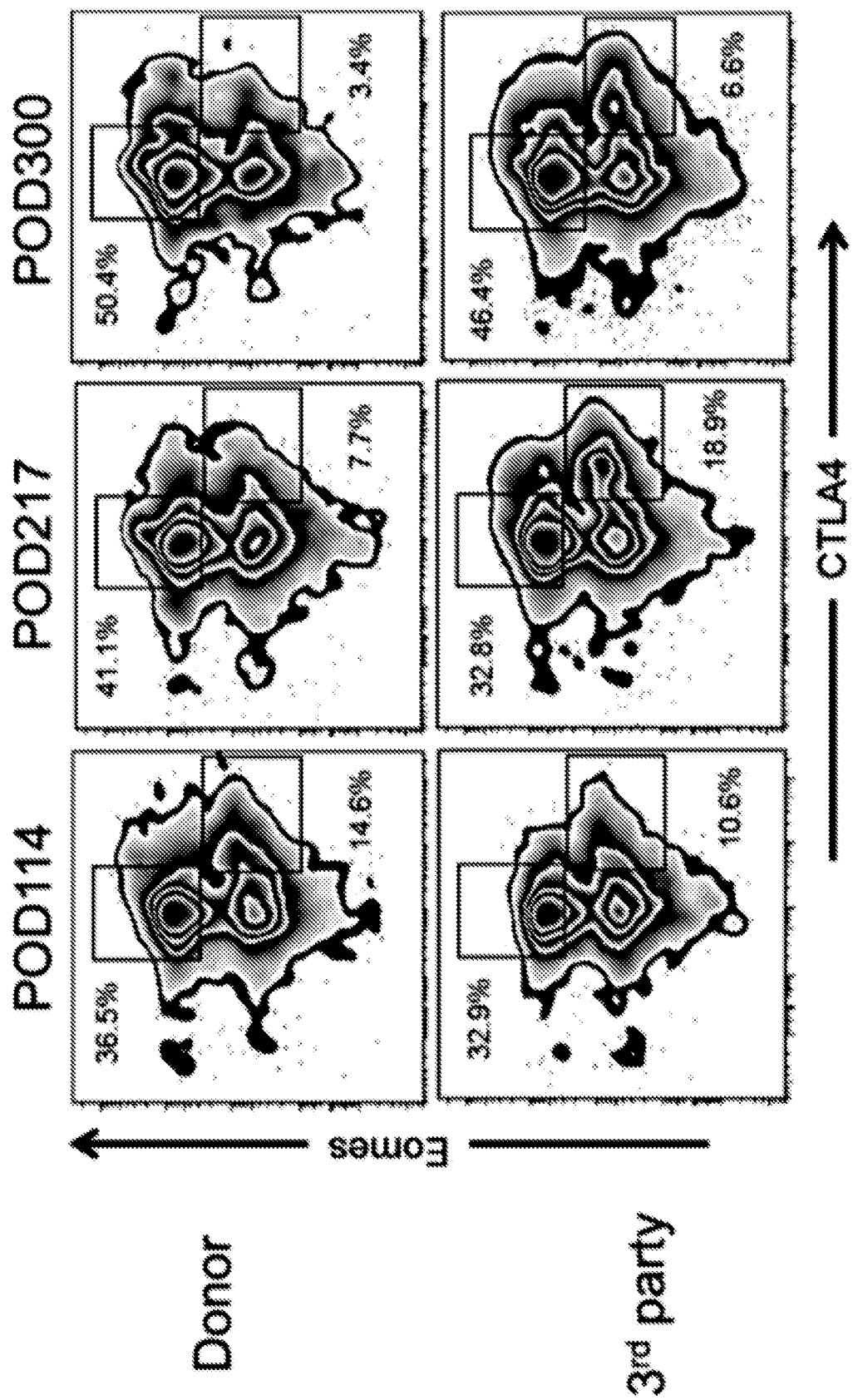
FIG. 8: Gradual decrease in donor-specific $Eomes^{lo}CTLA4^{hi}$ and increase in donor-specific $Eomes^{hi}CTLA4^{lo}CD8^+$ Tcm following withdrawal of immunosuppression in a long-surviving DCreg-infused renal allograft recipient. In a renal allograft recipient in the DCreg group that exhibited markedly prolonged transplant survival (300 days) the incidences of $Eomes^{lo}CTLA4^{hi}$ CD8+T cells following stimulation with either donor or third party cells, diminished progressively between days 114, 217 and 300 (the time of rejection) post-transplant Immunosuppression was stopped at day 180.

Donor-Specific Eomes$^{lo}$CTLA4$^{hi}$ CD8$^+$ Tcm in an Allograft Recipient Given DCreg Infusion and with Markedly Prolonged Graft Survival The foregoing observations regarding CD8$^+$ Tcm in groups of rhesus renal allograft recipients (FIG. 7) were made 1-2 months post-transplant. It was next investigated whether the elevated frequency of Eomes$^{lo}$CTLA4$^{hi}$ CD8$^+$ Tcm in recipients given DCreg might persist beyond 2 months, particularly following withdrawal of immunosuppression (that was stopped at 6 months). One graft in the DCreg group survived 300 days post-transplant. In this monkey, the frequencies of Eomes$^{lo}$CTLA4$^{hi}$ CD8$^+$ Tcm were 25.4% pre-transplant and 24.2% on POD28, while a gradual decrease to 14.6%, 7.7% and 3.4% was observed on POD 114, 217 and 300, respectively. In parallel, there were concomitant reductions in Eomes$^{hi}$CTLA4$^{lo}$ CD8$^+$ Tcm from 31.3% pre-transplant to 26.1% on POD28 (FIG. 8), followed by gradual increases to 36.5%, 41.1% and 50.4% on POD 114, 217 and 300, respectively. There was also an increase in Eomes$^{hi}$CTLA4$^{lo}$ CD8$^+$ Tcm in response to third party stimulation on POD300. Although from only one monkey, these data are consistent with in vitro findings (FIG. 4) regarding an inverse correlation between CTLA4 and Eomes expression by proliferating alloreactive CD8$^+$ Tcm.

Discussion

Pre-existing alloreactive Tmem are considered a major barrier to the induction of allograft tolerance (Valujskikh and Li, J Am Soc Nephrol 18(8):2252-2261, 2007; Ford and Larsen, Curr Opin Organ Transplant 15(4):405-410, 2010; Valujskikh, Am J Transplant 6(4):647-651, 2006; Lakkis and Sayegh, J Am Soc Nephrol 14(9):2402-2410, 2003). As Tmem require less co-stimulation compared to naïve T cells (Jameson and Masopust, Immunity 31(6):859-871, 2009; Valujskikh et al., Am J Transplant 2(6):501-509, 2002; Croft et al., J Immunol 152(6):2675-2685, 1994), alloreactive Tmem are thought to play a fundamental role in CB-resistant rejection (Trambley et al., J Clin Invest 104(12):1715-1722, 1999; Zhai et al., J Immunol 169(8):4667-4673, 2002; Farber, Am J Transplant 11(1):8-9, 2011) and preclude CB-induced tolerance (Farber, Am J Transplant 11(1):8-9, 2011; Ford et al., Transplantation 87(9 Suppl):S69-74, 2009).

Despite major advances in clinical organ transplantation, an important limitation remains patients' lifelong dependency on immunosuppressive drugs, with increased risk of morbidity and mortality (Lechler et al., Nat Med 11(6):605-613, 2005). Therapeutic regimens that allow the reduction or complete withdrawal of immunosuppression are most likely to result in long-term regulation of donor-reactive Tmem. CTLA4Ig (belatacept), a chimeric fusion protein that blocks the B7-CD28 pathway was approved by the FDA in 2011 for use in kidney transplantation. Compared to calcineurin inhibitors, use of CTLA4Ig has been associated with higher rates of acute cellular rejection in renal transplant patients, despite superior renal function (Vincenti et al., Am J Transplant 10(3):535-546, 2010).

The T-box transcription factors T-box expressed in T cells (T-bet) and Eomes are considered master regulators of CD8$^+$ Tmem differentiation and function (Pearce et al., Science 302(5647):1041-1043, 2003; Intlekofer et al., Nat Immunol 6(12):1236-1244, 2005; Angelosanto and Wherry, Immunol Rev 236:167-175, 2010; Li et al., PLoS One 8(6):e67401, 2013). Both T-bet and Eomes have cooperative and redundant roles in CD8$^+$ T cell function, but they also have distinctive roles in CD8$^+$ Tmem development. Eomes plays a critical role in long-term survival of Ag-specific Tcm (Banerjee et al., J Immunol 185(9):4988-4992, 2010). In rodents, Eomes is upregulated in early Teff, where its expression increases as T cells progress from an effector to a memory phenotype (Banerjee et al., J Immunol 185(9): 4988-4992, 2010; Pipkin et al., Immunity 32(1):79-90, 2010; Joshi et al., J Immunol 187(8):4068-4076, 2011). Additionally, Eomes knockouts are deficient in long-term formation and homeostatic renewal of Tmem (Intlekofer et al., Nat Immunol 6(12):1236-1244, 2005; Banerjee et al., J Immunol 185(9):4988-4992, 2010; Kaech et al., Cell 111(6):837-851, 2002).

The role of Eomes in the differentiation, regulation and maintenance of donor-specific Tmem in allograft recipients has hitherto not been examined. Furthermore, the expression of Eomes by Tn and Tmem in NHP has not previously been reported. The expression of Eomes by alloreactive CD4$^+$ and CD8$^+$ T cells was examined in normal monkeys and it was found that CD8$^+$ T cells expressed significantly higher levels than CD4$^+$ T cells. Similarly to humans (McLane et al., J Immunol 190(7):3207-3215, 2013), Tcm expressed the highest levels of Eomes compared to Tn, Tem and Teff. These observations indicate that Eomes plays a role in the development of donor-reactive CD8$^+$ Tmem after transplantation.

It has been reported that CTLA4 may reduce Eomes expression by CD8$^+$ T cells (Hegel et al., Eur J Immunol 39(3):883-893, 2009). In the current study, Eomes and CTLA4 expression by rhesus alloreactive CD8$^+$ T cells was evaluated. Following allostimulation, CD8$^+$ T cells upregulated both CTLA4 and Eomes expression. However, CD28 CB with CTLA4Ig during allostimulation did not reduce Eomes expression on CD8$^+$ T cells, despite efficient inhibition of T cell proliferation and significant reduction in CTLA4 expression. Following allostimulation, all proliferating CD4$^+$T cells exhibited low Eomes but high CTLA4 expression. In contrast, proliferating CD8$^+$T cells comprised two distinct populations, one with high and one with low Eomes expression. CTLA4 expression by Eomes$^{hi}$CD8$^+$T cells was lower than that by Eomes$^{lo}$ CD8$^+$ T cells, suggesting an inverse relationship between CTLA4 and Eomes expression.

In correlation, a significant increase in Eomes$^{lo}$CTLA4$^{hi}$CD8$^+$ T cells was observed following allostimulation, compared to Eomes$^{hi}$CTLA4$^{lo}$ or Eomes$^{lo}$CTLA4$^{lo}$ T cells. Furthermore, about 70% of these Eomes$^{lo}$CTLA4$^{hi}$ CD8$^+$ T cells were Tcm. In the presence of CTLA4Ig, there was a reduction in the Eomes$^{lo}$CTLA4$^{hi}$ population, with minimal effect on Eomes$^{hi}$CTLA4$^{lo}$T cells. These observations indicate that blocking CD28 co-stimulation maintains alloreactive T cells with high Eomes levels, while reducing those with high CTLA4 expression.

Regulatory immune cell therapy offers considerable potential for the development of protocols that may promote transplant tolerance (Bluestone et al., Nat Rev Immunol 7(8):650-654, 2007; Morelli and Thomson, Nat Rev Immunol 7(8):610-621, 2007; Lombardi et al., Immunotherapy 3(4 Suppl):28-31, 2011; Wood et al., Nat Rev Immunol 12(6):417-430, 2012; Geissler and Hutchinson, Curr Opin Organ Transplant 18(4):408-415, 2013; Hutchinson et al., Transfusion 54(9):2336-2343, 2014). DC are uniquely well-equipped, professional Ag-presenting cells that can promote Ag-specific tolerance (Banchereau and Steinman, Nature 392(6673):245-252, 1998; Steinman et al., Annu Rev Immunol 21:685-711, 2003; Ezzelarab and Thomson, Semin Immunol 23(4):252-263, 2011; Steptoe and Thomson, Clin

*Exp Immunol* 105(3):397-402, 1996; Stenger et al., *Blood* 119(22):5088-5103, 2012) based on their state of maturation. Furthermore, DC can regulate Tmem responses (Nasreen et al., *Eur J Immunol* 40(7):2016-2025, 2010; Anderson et al., *J Leukoc Biol* 84(1):124-133, 2008; Kenna et al., *J Immunol* 184(2):598-606, 2010). DCreg are considered promising cellular therapeutic agents to promote clinical transplant tolerance (Morelli and Thomson, *Nat Rev Immunol* 7(8):610-621, 2007; Ezzelarab and Thomson, *Semin Immunol* 23(4):252-263, 2011; van Kooten et al., *Transplantation* 91(1):2-7, 2011; Riquelme et al., *Transplant Res* 1(1):17, 2012; Beriou et al., *Curr Opin Organ Transplant* 17(1):42-47, 2012; Vassalli, *J Transplant* 2013:761429, 2013). It was previously reported that a single infusion of donor-derived DCreg, one week before transplantation, combined with CD28 CB using CTLA4Ig, can prolong renal allograft survival (Ezzelarab et al., *Am J Transplant* 13(8):1989-2005, 2013). In these graft recipients given DCreg, selective downregulation of circulating donor-reactive Tmem and enhanced Treg/Tmem ratios in peripheral blood were observed. This was associated with their enhanced expression of co-inhibitory CTLA4 and PD1 following stimulation with donor, but not third party alloAg (Ezzelarab et al., *Am J Transplant* 13(8):1989-2005, 2013).

While PD1 and CTLA4 are considered markers of T cell exhaustion, they have distinct inhibitory effects on T cell activation (Kaufmann and Walker, *J Immunol* 182(10):5891-5897, 2009). Tumors evade adaptive immune responses through upregulation of CTLA4 and PD1, where co-expression of CTLA4 and PD1 is associated with significant dysfunction of Ag-specific T cells (Duraiswamy et al., *Cancer Res* 73(12):3591-3603, 2013). CTLA4 expression, with or without PD1, is associated with reduced proliferation and cytokine production by $CD8^+$ T cells. Furthermore, blocking of CTLA4 and PD1 interaction in vivo upregulates T-bet and Eomes in $CD8^+$ T cells (Duraiswamy et al., *Cancer Res* 73(12):3591-3603, 2013) that are required for in anti-tumor responses (Zhu et al., *J Immunol* 185(6):3174-3183, 2010).

These observations indicate that when Tmem encounter donor Ag following their infiltration of the graft, they upregulate PD1 and CTLA4 that, in turn, inhibit donor-reactive Tmem activation. To address this, PD-1 and CTLA4 expression by $CD8^+$ T cells were examined in kidney allografts 28 days post-transplant. It was determined that $CD8^+$ T cells infiltrating the graft displayed stronger CTLA4 and PD1 expression in the DCreg group than in the control group that did not receive regulatory cell infusion. Since this enhanced expression of CTLA4 and PD1 by donor-reactive Tmem may underlie improved graft survival in the cell therapy group, it was explored whether upregulation of these co-inhibitory molecules are associated with regulation of donor-specific Tmem responses in the monkeys given DCreg infusion. The frequency of $Eomes^{lo}CTLA4^{hi}$ $CD8^+$ Tcm in allograft recipient monkeys in response to donor stimulation before and after transplant was ascertained. In correlation with in vitro observations, the frequency of $Eomes^{lo}CTLA4^{hi}$ $CD8^+$ Tcm in response to donor stimulation was reduced significantly in the CTLA4Ig-treated monkeys (control group) post-transplant. By contrast, the frequency of $Eomes^{lo}CTLA4^{hi}$ $CD8^+$ Tcm was increased modestly after transplantation in the CTLA4Ig-treated monkeys given DCreg. More importantly, the mean percentages and absolute numbers of $Eomes^{lo}CTLA4^{hi}$ $CD8^+$ Tcm, a phenotype that suggests low persistence/exhaustion, was higher in the DCreg group than in the control group post-transplant.

These observations provide further insight to the limitations of CD28 CB in organ transplantation. Significant reduction of the co-inhibitory receptor CTLA4 by alloreactive Tmem in the presence of CTLA4Ig in vitro and in CTLA4Ig-treated graft recipients post-transplant, together with no reduction in Eomes expression by donor-reactive Tmem, may be a key factor in the development of CB resistance. While CTLA4Ig reduces effector T cell responses against donor Ag efficiently, this may be achieved at the expense of regulatory mechanisms that favor donor-specific Treg and attenuate donor-specific Tmem, resulting in increased rates of acute cellular rejection, as observed in renal allograft recipients (Vincenti et al., *Am J Transplant* 10(3):535-546, 2010; Pestana et al., *Am J Transplant* 12(3): 630-639, 2012).

The role of Eomes in the development of alloreactive Tmem after transplantation has until now, not been ascertained. As Eomes plays a critical role in the maintenance of Tcm (Banerjee et al., *J Immunol* 185(9):4988-4992, 2010), its reduced expression is believed to attenuate donor-reactive Tcm after transplantation. This, together with the upregulation of CTLA4 by Tmem that was demonstrated in graft recipients given DCreg, might further mitigate anti-donor T cell responses. Taken together, these observations indicate that DCreg infusion before renal transplantation will help preserve donor-specific Tmem regulation that is compromised with use of CD28 CB.

Example 3: Characterization of Human $CD8^+$ Eomes-Positive T Cells

Figure 10:
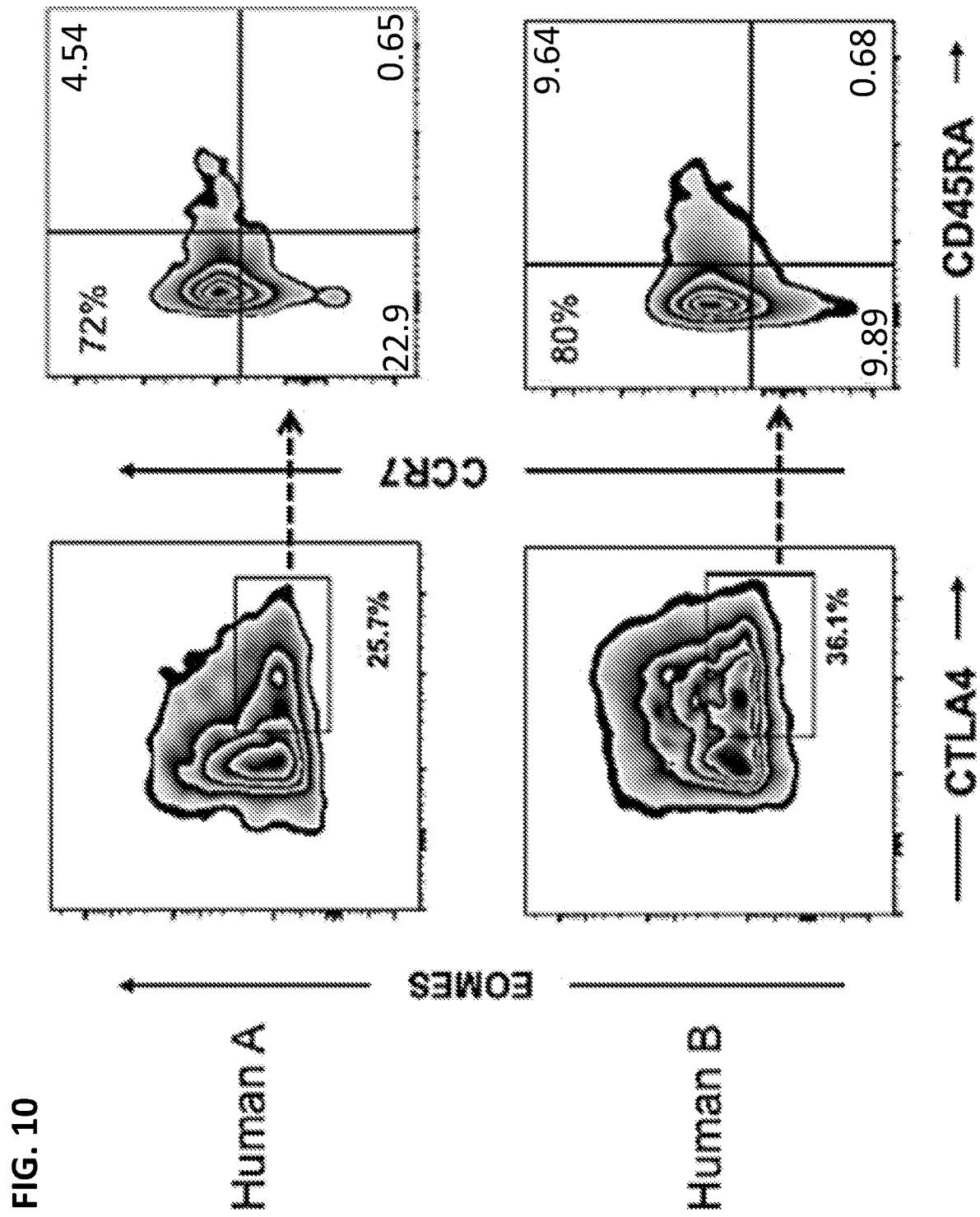
FIG. 10: $Eomes^{low}CTLA4^{high}$ activated human CD8+T cells exhibit a higher incidence of central memory T cells. Human peripheral blood mononuclear cells obtained from 2 healthy human subjects were activated for 4 days using anti-CD2/CD3/CD28 beads. After activation, the CD8+T cells were stained for Eomes and CTLA4. Additionally, the $Eomes^{low}CTLA4^{high}$ population was further characterized into memory and naïve phenotype based on their differential expression of CD45RA and CCR7. In both human subjects, activated CD8+ $Eomes^{low}CTLA4^{high}$ cells exhibited increased incidences of CCR7+CD45RA− central memory T cells.

Human PBMCs obtained from two healthy human subjects were activated for 4 days using anti-CD2/CD3/CD28 beads. After activation, the $CD8^+$T cells were stained for Eomes and CTLA4. Additionally, the $Eomes^{low}$ $CTLA4^{high}$ population was further characterized into memory and naïve phenotype based on their differential expression of CD45RA and CCR7. In both human subjects, activated $CD8^+$ $Eomes^{low}$ $CTLA4^{high}$ cells exhibited increased incidences of $CCR7^+$ $CD45RA^-$ central memory T cells (FIG. 10).

Figure 11:
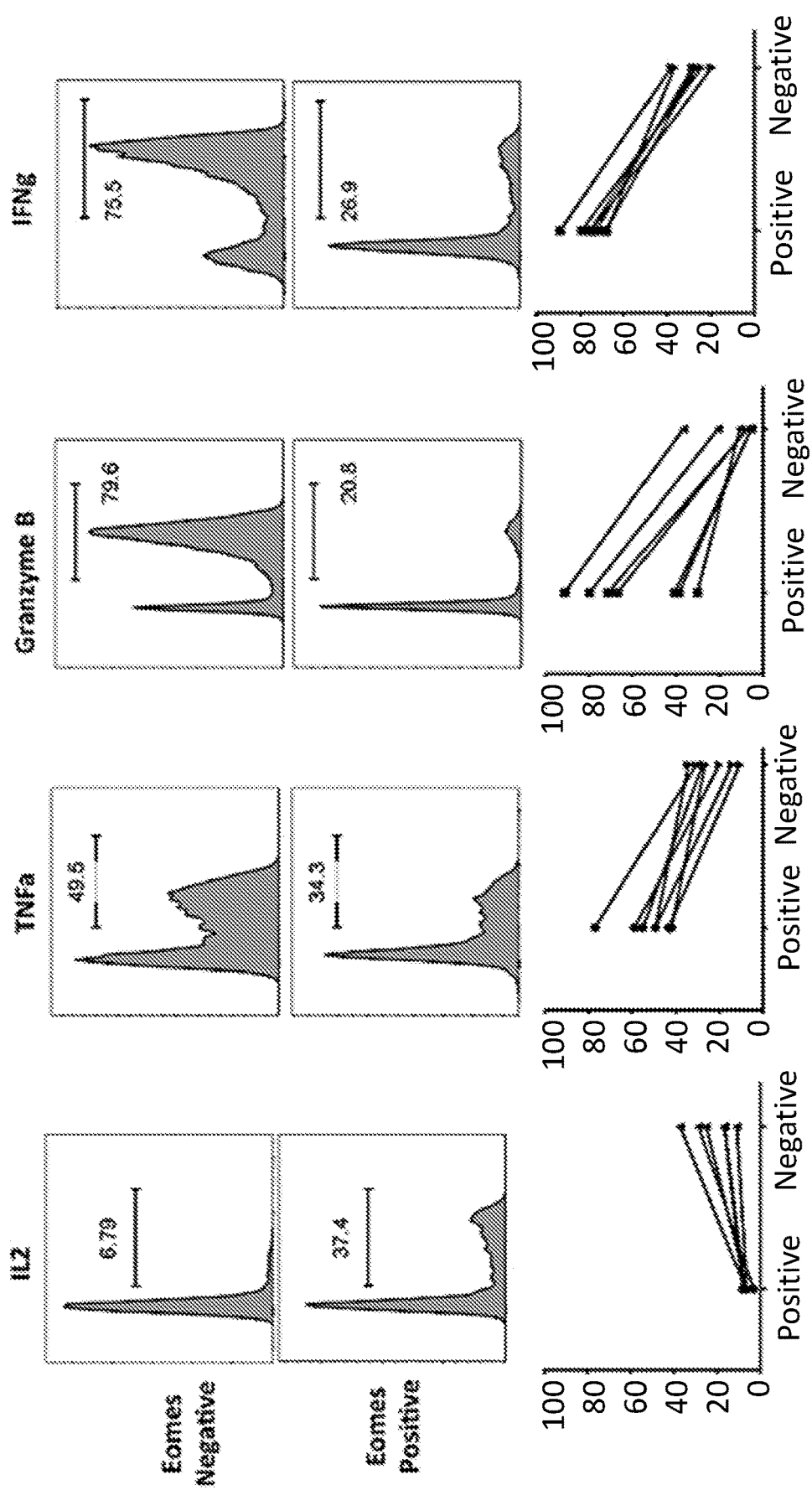
FIG. 11: Human CD8+ Eomes-positive T cells express higher levels of effector cytokines. Human peripheral blood mononuclear cells were obtained from seven healthy volunteers. CD8+T cells were evaluated for the expression of effector cytokines interleukin-2 (IL-2), tumor necrosis factor alpha (TNFα), granzyme B, and interferon gamma (IFNγ).

To evaluate expression of effector cytokines by $CD8^+$ Eomes-positive T cells, human PBMCs were obtained from seven healthy volunteers. $CD8^+$T cells were evaluated for the expression of IL-2, TNFα, granzyme B, and IFNγ. While Eomes $CD8^+$T cells expressed lower levels of IL-2, they expressed significantly higher levels of TNFα, granzyme B, and IFNγ (FIG. 11).

To evaluate the degree of Eomes expression by CD8+T cells, PBMCs were obtained from healthy human volunteers and $CD8^+$T cells were stained for Eomes by flow cytometry (FIG. 12A, left). Gating was based on isotype control. Data from 4 different human subjects are presented in FIG. 12A. Eomes expression by human T cells stimulated with allogeneic T cell-depleted PBMC in co-culture for 5 days was also evaluated. Responder T cells were CFSE-labeled before co-culture and percent proliferation was determined by CFSE dye dilution (FIG. 12B). The results demonstrated that human exhibit variable degrees of Eomes expression by $CD8^+$ T cells, particularly after allogeneic antigen stimulation.

In summary, these observations indicate that, in humans (as well as in monkeys), memory T cells with low Eomes expression observed during ex vivo peripheral blood CD8+T cell responses to donor cell stimulation can be used as a biomarker to determine/predict immune reactivity/tolerance of the recipients to their transplant; and safe/successful weaning of immunosuppression.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of determining the risk of allograft rejection in a subject who has received an allograft, comprising:
   obtaining a peripheral blood mononuclear cell (PBMC) sample from the subject before the subject received the allograft and obtaining a PBMC sample from the subject after the subject received the allograft;
   isolating memory T cells from the PBMC samples, wherein isolating memory T cells comprises isolating cells that express at least one memory T cell marker selected from CD95 and CD45RO;
   measuring expression of Eomesodermin (Eomes) in the memory T cells isolated from the PBMC samples;
   detecting an increase in expression of Eomes in the memory T cells isolated from the sample obtained after the subject received the allograft compared to expression of Eomes in the memory T cells isolated from the sample obtained before the subject received the allograft, thereby determining an increased risk for allograft rejection in the subject; and
   modifying a treatment administered to the subject with the increased risk for allograft rejection after receiving the allograft relative to a current therapy, wherein the treatment administered to the subject comprises an immunosuppressive therapy and the modifying comprises increasing a dose and/or frequency of the immunosuppressive therapy relative to a value administered before receiving the allograft, administering an alternative immunosuppressive therapy relative to the immunosuppressive therapy administered before receiving the allograft, or administering an additional immunosuppressive therapy to the subject.

2. The method of claim 1, wherein isolating memory T cells further comprises detecting the absence of expression of at least one naïve or effector T cell marker.

3. The method of claim 1, wherein measuring expression of Eomes in the memory T cells isolated from the samples comprises simultaneously detecting expression of Eomes and the at least one memory T cell marker selected from CD95 and CD45RO.

4. The method of claim 3, further comprising simultaneously detecting the absence of expression of at least one naïve or effector T cell marker.

5. The method of claim 2, wherein the at least one naïve or effector T cell marker is selected from CD28 and CD45RA.

6. The method of claim 1, wherein the allograft comprises kidney tissue.

7. A method of treating a subject who has received an allograft, comprising:
   administering an immunosuppressive therapy to the subject;
   providing a peripheral blood mononuclear cell (PBMC) sample obtained from the subject before administration of the immunosuppressive therapy and a PBMC sample obtained from the subject after administration of the immunosuppressive therapy;
   isolating memory T cells from the PBMC samples, wherein isolating memory T cells comprises isolating cells that express at least one memory T cell marker selected from CD95 and CD45RO;
   detecting an increase in expression of Eomesodermin (Eomes) in the memory T cells isolated from the sample obtained after administration of the immunosuppressive therapy compared to the sample obtained before administration of immunosuppressive therapy; and
   modifying the immunosuppressive therapy administered to the subject, wherein modifying the immunosuppressive therapy comprises increasing the dose and/or frequency of the immunosuppressive therapy administered to the subject, or administering to the subject an alternative or additional immunosuppressive therapy.

8. The method of claim 7, wherein isolating memory T cells further comprises detecting the absence of expression of at least one naïve or effector T cell maker.

9. The method of claim 7, wherein detecting expression of Eomes in the isolated memory T cells comprises simultaneously detecting expression of Eomes and the at least one memory T cell marker selected from CD95 and CD45RO.

10. The method of claim 9, further comprising simultaneously detecting the absence of expression of at least one naïve or effector T cell marker.

11. The method of claim 10, wherein the at least one naïve or effector T cell marker is selected from CD28 and CD45RA.

12. The method of claim 7, wherein the allograft comprises kidney tissue.

* * * * *